United States Patent
Yu

(10) Patent No.: US 9,353,213 B2
(45) Date of Patent: May 31, 2016

(54) FUNCTIONAL NORBORNANYL ESTER DERIVATIVES, POLYMERS AND PROCESS FOR PREPARING SAME

(71) Applicant: Hui Yu, Kansas City, MO (US)

(72) Inventor: Hui Yu, Kansas City, MO (US)

( * ) Notice: Subject to any disclaimer, the term of this patent is extended or adjusted under 35 U.S.C. 154(b) by 53 days.

(21) Appl. No.: 14/530,821

(22) Filed: Nov. 2, 2014

(65) Prior Publication Data

US 2016/0122469 A1     May 5, 2016

(51) Int. Cl.
| | |
|---|---|
| *C07C 69/753* | (2006.01) |
| *C07C 69/757* | (2006.01) |
| *C08F 222/10* | (2006.01) |
| *C08F 232/08* | (2006.01) |
| *C08G 63/137* | (2006.01) |
| *C07C 69/734* | (2006.01) |
| *C07C 67/08* | (2006.01) |

(52) U.S. Cl.
CPC .............. *C08G 63/137* (2013.01); *C07C 67/08* (2013.01); *C07C 69/734* (2013.01); *C07C 2102/42* (2013.01)

(58) Field of Classification Search
CPC ... C07C 69/753; C07C 69/757; C08F 222/10; C08F 232/08; C08G 63/137

USPC .......... 524/356, 553, 599, 366, 379; 526/281; 528/307

See application file for complete search history.

(56) References Cited

U.S. PATENT DOCUMENTS

2006/0105269 A1*   5/2006   Khojasteh ............. C08F 220/24
                                                                                                   430/270.1

OTHER PUBLICATIONS

Mamedov et al. "Synthesis of Diester by Addition of Acids to 5-Alkoxycarbonylnorborn-2-ene and Related 5-Methyl Derivatives", Russ. J. Gen. Chem., 2012, vol. 82, No. 4, pp. 659-662.*
STIC Search—May 1, 2014.*

* cited by examiner

*Primary Examiner* — Ling Choi
*Assistant Examiner* — Ronald Grinsted

(57) ABSTRACT

This invention relates to the new functional norbornanyl ester derivative and/or polymer compositions which are easily obtainable by reacting the Diels-Alder adduct of appropriate dienes and dienophiles with carboxylic acids. In particular, this invention relates to a new process for making cyclic chemical raw materials suitable for production coating, ink, adhesive, plasticizer, thermoplastic or thermosetting plastic and functional polymers.

10 Claims, No Drawings

FUNCTIONAL NORBORNANYL ESTER DERIVATIVES, POLYMERS AND PROCESS FOR PREPARING SAME

CROSS-REFERENCE TO RELATED APPLICATION

This application is a divisional of U.S. application Ser. No. 13/481,739, filed on May 25, 2012, now allowed, the disclosure is incorporated herein by reference in its entirety.

US PATENT REFERENCES

| | | | |
|---|---|---|---|
| 4,948,866 | August 1990 | Liu | 528/272 |
| 4,292,221 | September 1973 | Malatesta | 260/23.7 |
| 5,214,125 | May 1993 | Mitani | 528/344 |
| 5,252,682 | October 1993 | Bayha | 525/445 |
| 5,427,881 | June 1995 | Sacripante | 430/109 |
| 6,517,994 | February 2003 | Watanabe | 430/270.1 |
| 6,309,719 | October 2001 | Schiraldl | 428/35.7 |
| 6,384,151 | May 2002 | Matsukawa | 525/445 |
| 6,825,374 | November 2004 | Shiomi | 560/116 |
| 6,939,997 | September 2005 | Lappe | 568/817 |
| 7,033,676 | April 2006 | Blum | 428/480 |
| 7,557,148 | July 2009 | Nishiguchi | 523/122 |
| 2009/0012324 | January 2009 | Choi | 560/107 |

-continued

| | | | |
|---|---|---|---|
| 2010/0094030 | April 2010 | Bell | 549/523 |
| 2011/0257317 | October 2011 | Baugh | 524/308 |

FOREIGN PATENT REFERENCES

| | | |
|---|---|---|
| WO | 2012035874 | March 2012 |
| GB | 1369370 | September 1972 |
| JP | 2007022962 | February 2007 |
| JP | 2003171346 | June 2003 |

OTHER REFERENCES

"A General Polymerization Method Using Hydroalkoxyation and Hydrocarboxylation Reactions Catalyzed by Triflic Acid", Robert T. Mathers, Macromolecules, vol. 41, January 2008, pp. 524-526.

BACKGROUND OF THE INVENTION

1. Field of the Invention

The present invention relates to novel functionalized norbornanyl ester derivatives and/or polymers composition, which are produced by reacting substituted norbornenes with a carboxylic acid. In particular, this invention relates to a novel process for making bicyclic chemical raw material and polymeric material from Diels-Alder adduct, which is easily obtained by reacting diene with dienophile.

The invention specifically provides new functional norbornanyl ester derivative compositions represented by the general Formula-1:

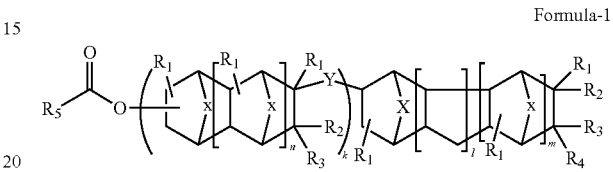

Formula-1

The invention also provides new composition of polymer or oligomer comprising the units of norbornanyl ester type represented by the general Formula-2:

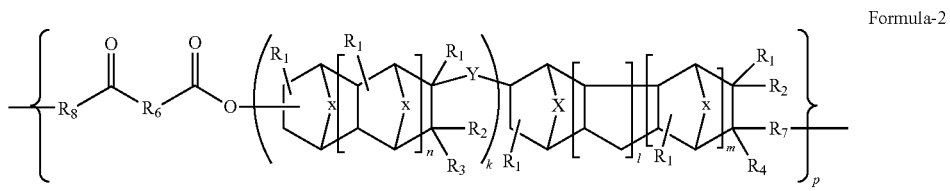

Formula-2

The functional norbornanyl ester derivatives and polymer compositions represented by the Formula-1 and Formula-2 are prepared from norbornenyl derivative by Diels-Alder reaction. The norbornenyl derivative represented by the general Formula-3:

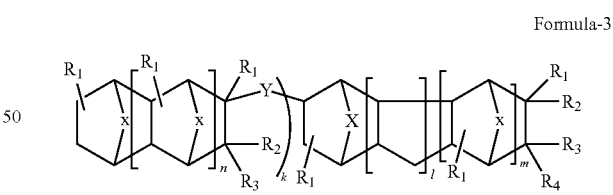

Formula-3

In the Formula-1, Formula-2, Formula-3, $R_1$ is a hydrogen atom, a methyl, or a hydroxymethyl group and $R_2$, $R_3$, and $R_4$ are the same or different from each other and are independently selected from the group consisting of hydrogen; halogen; hydroxyl; acid (—C(O)OH); ester (—C(O)OR$_a$); formate (—OC(O)H); acid halide (—C(O)Z); aldehyde (—C(O)H); ketone (—C(O)R$_a$); nitro (—NO$_2$); carboxamide (—C(O)NR$_a$R$_b$); amine (—NR$_a$R$_b$); silicone (—SiR$_a$R$_b$R$_c$); cyano (—CN); isocyanate (—NCO); alkoxy (—OR$_a$); phosphonate (—P(O)R$_a$R$_b$); unsubstituted or substituted $C_1$-$C_{100}$ alkyl group, unsubstituted or substituted $C_2$-$C_{100}$ alkenyl group, unsubstituted or substituted $C_2$-$C_{100}$ alkynyl group, unsubstituted or substituted $C_3$-$C_{100}$ cycloalkyl group, unsubstituted or substituted $C_6$-$C_{100}$ aryl group, provided that when it is substituted with one or more substituent group, the substituent group may be carboxyl, hydroxyl, thiol, halogen, ester, amine, amide, imide, isocyanate, alkyl, alkenyl, alkynyl, haloalkyl, haloalkenyl, haloalkynyl, aryl, haloaryl, aralkyl, haloaralkyl, alkoxy, haloalkoxy, halocarbonyloxy, aryloxy, haloaryloxy, silyl, siloxy, glycidoxy, heterocyclo, carbonate, carboxylate, or quaternary ammonium; with the proviso that at least one of $R_2$, $R_3$, and $R_4$ is a polar functional group containing at least one atom selected from the group consisting of oxygen, nitrogen, phosphorus, sulfur, silicon and boron; $R_2$, $R_3$, and $R_4$ may be an acid anhydride group (—C(O)—O—C(O)—) or a imide groups (—C(O)—NR$_d$—C(O)—) formed by being bonded to each other when they are the functional groups;

$R_5$ is a substituted alkane, alkene, or cycloaliphatic group wherein at least one substituent group is a carboxyl or ester group;

X represents oxygen, $CH_2$, or $CH_2$—$CH_2$;

k is an integer of 0 to 100; l is an integer 0 to 1; m and n both represent an integer 0 to 5; p is an integer 1 to 1000;

Y is a bridge member selected from the group consisting of (—C(O)O—), (—$R_6$—), (—$R_7$C(O)O—), (—C(O)O$R_7$O—), (—C(O)O$R_7$OC(O)—), (—O—), (—O$R_7$O—), (—$R_7$OC(O)O$R_8$—), (—$R_7$C(O)O$R_8$—), and (—$R_7$C(O)$R_8$—);

$R_a$, $R_b$ and $R_c$ are independent hydrocarbyl or substituted hydrocarbyl,

Rd is a hydrocarbyl group substituted with hydroxyl, alkoxy, alkenyl, amine, amide or imide group;

Z is a halogen atom;

$R_6$, $R_7$ and $R_8$ are divalent organic groups and may be substituted or unsubstituted alkanes, alkenes, cycloaliphatic groups.

This invention also provides the process of producing the norbornenyl derivative of Formula-3; the norbornanyl ester derivative of Formula-1, the norbornenyl polymer of Formula-2 and a norbornanyl lactone derivative or polymer.

2. Description of the Related Art

Norbornane based alicyclic derivatives and polymers have great economic significance as important intermediate or polymeric material for the chemical industry. They are particularly attractive because their bulky, bridged cyclic skeleton affords unique properties such as better adhesion, low density, high rigidity, good surface hardness, high glass transition temperatures, better transparency, heat and chemical resistance, low birefringence, low surface energy, optical clarity, low shrinkage, low moisture absorption, low hygroscopy, and improved crystallinity. These compounds and the resulting polymeric materials are used in various articles ranging from optical materials, low-dielectric IT materials, coating, ink, and medicinal materials to high performance engineering plastics. Accordingly, today, demand in supply of norbornane derivatives or polymers have steadily increased. However, the application of norbornane cyclic derivatives and polymers depends to a high degree on the availability and price of the bicyclic raw materials. Most bicyclic compounds used in the industry are made from hydrogenation or oxidization of Diels-Alder adducts obtained from dicyclopentadiene (DCPD) and other chemicals. There are some reports regarding preparation of norbornanyl derivatives and polymers. One method is hydrogenation of the norbornenyl derivative. For example, U.S. Pat. Nos. 4,948,866 and 6,309,719 as well as Japanese patent application 2007022962 reported the catalytic hydrogenation process of preparing alicyclic compounds.

Another method is oxidation of cyclic olefin. U.S. Pat. No. 5,214,125 and 20110257317 claim that alicyclic dicarboxylic acid can be produced by oxidizing a corresponding cyclic olefin and opening its ring with potassium permanganate or nitric acid. U.S. patent 20100094030 reported preparation of alicyclic diepoxides from norbornenyl derivatives with percarboxylic acid. In U.S. Pat. No. 6,939,997, dimethanolic derivatives of dicyclopentadiene are obtained by hydrogenating TCD-aldehydes, which are the hydroformylation products of dicyclopentadiene.

A polyester possessing a norbornane backbone and exhibiting excellent heat resistance and transparency can be prepared by hydroesterification of methyl formate with norbornene monomer in the presence of catalytic amounts of ruthenium complexes (WO 2012035874). Dicyclopentadiene monoesters are known. For example, see U.S. Pat. Nos. 7,033,676, 5,252,682. Generally, dicyclopentadiene monoesters are prepared by reacting maleic anhydride with dicyclopentadiene in the presence of water. Dicyclopentadiene maleic monoester can be used for production of unsaturated polyester resins as a chain end capping agent.

Substituted norbornanyl esters can be prepared from hydrocarboxylation reaction. These bicyclic compounds are normally produced by acid-catalyzed addition of the corresponding carboxylic acids to norbornenyl ring in the Diels-Alder adduct to form ester linkages. Many catalysts have been proposed, including metal trifluoromethanesulfonate (U.S. patent 20090012324), activated acidic clay (U.S. Pat. No. 7,557,148), triflic acid (Japanese patent application 2003171346; Macromolecules 2008, 41, 524-526). Lactone ring containing compounds such as 2,6-norbornane carbolactone-3-carboxylic acid can be prepared from 5-norbornene-2,3-dicarboxylic anhydride with 30% sulfuric acid as disclosed in U.S. Pat. No. 6,517,994.

The known processes for preparing norbornane derivatives by hydrogenation, oxidization, hydroalkoxylation, and hydrocarboxylation all require the presence of specific catalyst systems that are either unavailable in industry or environmentally and economically impractical. Alternatives to hydrogenation and oxidization methods are needed due to technical reasons as well as the supply shortage. However, there has been no report on the efficient preparation of ridged, bicyclic skeleton derivatives or polymers with hydrocarboxylation reaction. There is therefore a need for a simple and inexpensive process for preparing chemical raw materials or polymeric materials containing a bridged ring structure. A valuable process would avoid the use of a catalyst.

SUMMARY OF THE INVENTION

Norbornene derivatives are Diels-Alder adducts of dienophiles and dienes. These cyclic compounds have bridged, six-member ring with a double bond on one side. The bridged ring puts extra strain on the double bond, making it highly reactive for hydrocarboxylation, hydroalkoxylation, epoxidation, polymerization, and other reactions.

The first purpose of this invention is to incorporate a functional group into the double bond of the norbornene's strained cycloheptene structure, making a saturated bicyclic compound with a reactive group. The addition reaction between the Diels-Alder adduct and a multifunctional acid results in new norbornanyl derivatives substituted with saturated or unsaturated carboxyl or hydroxyl groups, which are useful as raw materials for fine chemical industry. Diels-Alder adducts may be obtained from appropriate dienes and dienophiles. It is also possible to first modify the Diels-Alder adduct to obtain a more active cycloheptene ring and subsequently react its active double bond with an appropriate polar group. The modification of Diels-Alder adducts provides a method to optimize the molecular structure of functional bicyclic compounds. In this way, the properties of products can easily be varied by changing both the structure of the Diels-Alder adducts and the structure of the multifunctional carboxylic acids. This new chemistry will provide great opportunities for industrial organic synthesis.

The second purpose of this invention is to obtain a novel functional polymer containing a polycyclic hydrocarbon skeleton.

The third purpose of this present invention is to provide a process of forming functional norbornenyl derivative, functional norbornanyl derivative and polymer and the polyester containing lactone structure. The process includes subjecting a norbornenyl derivative from Diels-Alder reaction and a multicarboxylic acid to an acid addition or hydroalkoxylation reaction. The acid addition of the norbornenyl derivative is processed in the absence of catalyst. This self-catalytic process eliminates the need to remove the catalyst and can be finished in a one-pot process.

The synthetic strategy of this invention includes three steps:

1. Synthesis of norbornenyl derivative by Diels-Alder reaction
2. Addition of carboxylic acid to norbornenyl derivative
3. Polymerization of functional norbornanyl ester derivative Step 1: Synthesis of Norbornenyl Derivative by Diels-Alder Reaction The formation of the substituted norbornenes by reacting a dienophile with a diene, such as cyclopentadiene, can be illustrated in the reaction below.

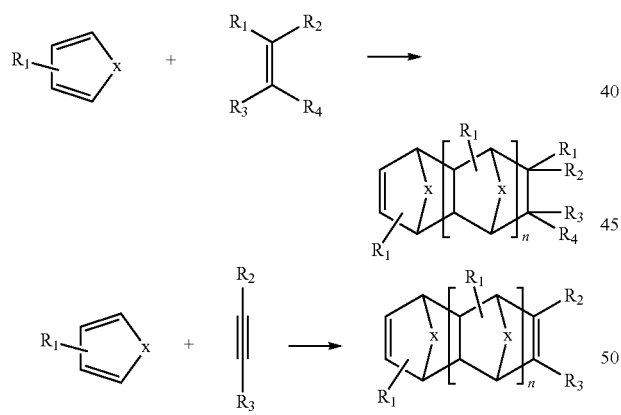

wherein the definitions of $R_{1-8}$, x and n are the same as those in Formula-1.

Step 2: Addition of Carboxylic Acid to Norbornenyl Derivative

The norbornenyl double bond reacts with a mono or multifunctional carboxylic compound to obtain a norbornanyl ester based cyclic compound containing a carboxylic acid or other reactive group. This step can be processed without a catalyst. The resulting product may be directly packaged as chemical raw material or used in the next step for polymer synthesis.

Addition of carboxylic acid to norbornenyl derivative can be illustrated in the reaction below.

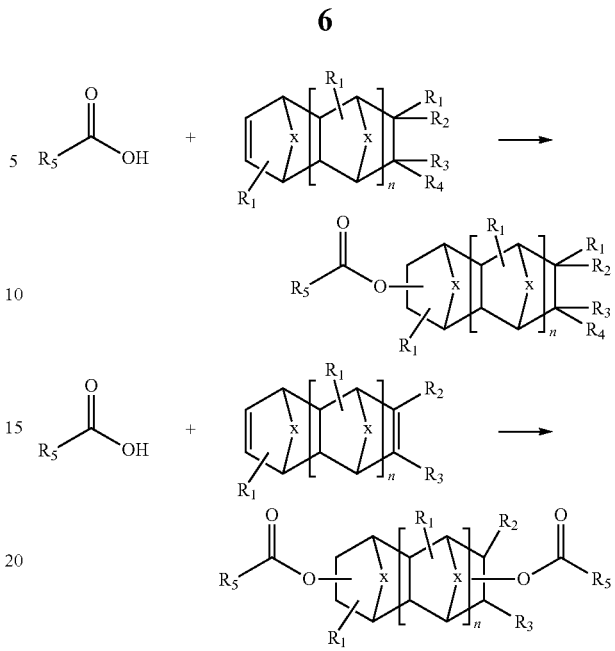

wherein the definitions of $R_{1-8}$, x and n are the same as those in Formula-1.

Step 3: Polymerization of Functional Norbornanyl Ester Derivative

The saturated or unsaturated carboxylic acid substituted norbornanyl ester derivative reacts with reactive compounds, which contain epoxy, isocyanate, carboxyl, anhydride, hydroxyl, amine or other functional groups, to produce functional polymer containing a bridged ring structure in the main or side chain.

Polymerization of functional norbornanyl ester derivative can be illustrated in the reaction below.

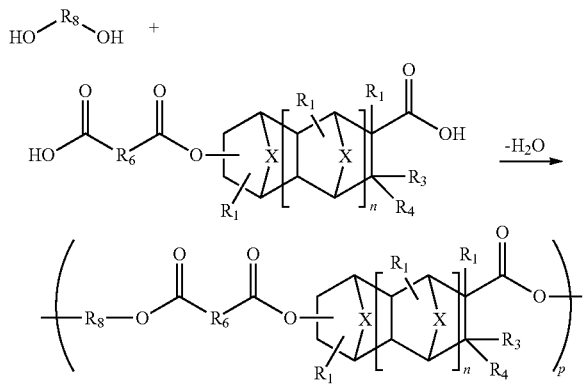

wherein the definitions of $R_{1-8}$, x, p and n are the same as those in the Formula-2

The mechanism of production of a polymer containing a bicyclic structure employed in the present invention is the addition of a carboxyl group of a multi carboxylic acid across norbornenyl double bonds of the norbornenyl carboxylic acid. The resulting norbornanyl multicarboxylic acid reacts with glycol or epoxy compound to form a polyester through an ester linkage. Since norbornenyl carboxylic acid can be prepared from cyclopentadiene and unsaturated acid with low cost and converted to norbornanyl dicarboxylic acid with multicarboxylic acid in a self-catalyzing one-pot process without external catalyst, the employment of this mechanism and process affords the user a great deal of flexibility in designing and synthesizing desired bicyclic polymer structures, such as polyester, polyamide, polyesterimide and polyesterether.

DETAILED DESCRIPTION OF THE PREFERRED EMBODIMENT

1: Norbornenyl Derivative Synthesis

Norbornenyl derivative can be purchased as commercial chemical or it prepared by a Diels-Alder reaction of a functional olefin with a cyclic diene to form a desired functional group substituted norbornenyl derivatives.

The diene is preferably selected from hydrocarbon dienes such as cyclic hydrocarbons, i.e. mono-cyclic or polycyclic, and non-cyclic hydrocarbon dienes, the latter being both straight chain and branched dienes. Preferably, the dienes are cyclic dienes commonly having at least 5 carbon atoms. The dienes may also be substituted with alkyls such as methyl, ethyl and the like. Examples of polycyclic hydrocarbon dienes are dicyclopentadiene and tricyclopentadiene. Examples of monocyclic hydrocarbon dienes are cyclopentadiene, alkyl substituted cyclopentadiene such as methyl cyclopentadiene, ethyl cyclopentadiene, etc. Substituted or unsubstituted furan also can be used for diene such as furfural alcohol, furaldehyde and furoic acid. Mixtures of the above mentioned dienes can also be used.

While the purity of the cyclopentadiene, dicyclopentadiene or the alkyl-substituted derivatives thereof does not need to be high, it is preferred that these compounds are present in an amount exceeding 80% by weight. For instance, a dicyclopentadiene mixture obtained as a by-product in cracking naphtha at elevated temperatures can be used.

Suitable dienophiles are basically all compounds that can undergo a Diels-Alder reaction with the diene. Preferred dienophiles include unsaturated organic acids, anhydrides and esters such as acrylic acid, methacrylic acid, (meth)acrylate esters, such as methyl acrylate, hexanediol dia(meth)crylate, trimethylolpropano tri(meth)acrylate, (meth)acrylic oligomer or polymer with (meth)acrylate side chain, acrylonitrile, acrolein, maleic acid, fumaric acid, itaconic acid, maleic anhydride and nadic anhydride; monoesters of maleic acid, monoesters of fumaric acid, monoester of itaconic acid, monoesters of nadic acid, esters of maleic acid, esters of fumaric acid, esters of nadic acid, ester of itaconic acid, include unsaturated polyester containing esters of maleic acid, esters of fumaric acid, esters of nadic acid, esters of itaconic acid, benzoquinone, vinyl kentones, such as methyl vinyl kentone, nitroalkenes, esters of acetylenedicarboxylic acid, like dimethyl ester of acetylenedicarboxylic acid, dibenzoacetylene, dicyano acetylene, fatty acid and ester of fatty acid.

Other dienophiles include substituted olefin such as norbornene, terpene, styrene, indene, nadic imide and maleimide. Each of the Diels-Alder adduct prepared from the above dienes and dienophiles can be used alone or in combination in the present invention. Accordingly, preferable examples of substituted norbornenyl derivatives according to the present invention are represented by the following general structures.

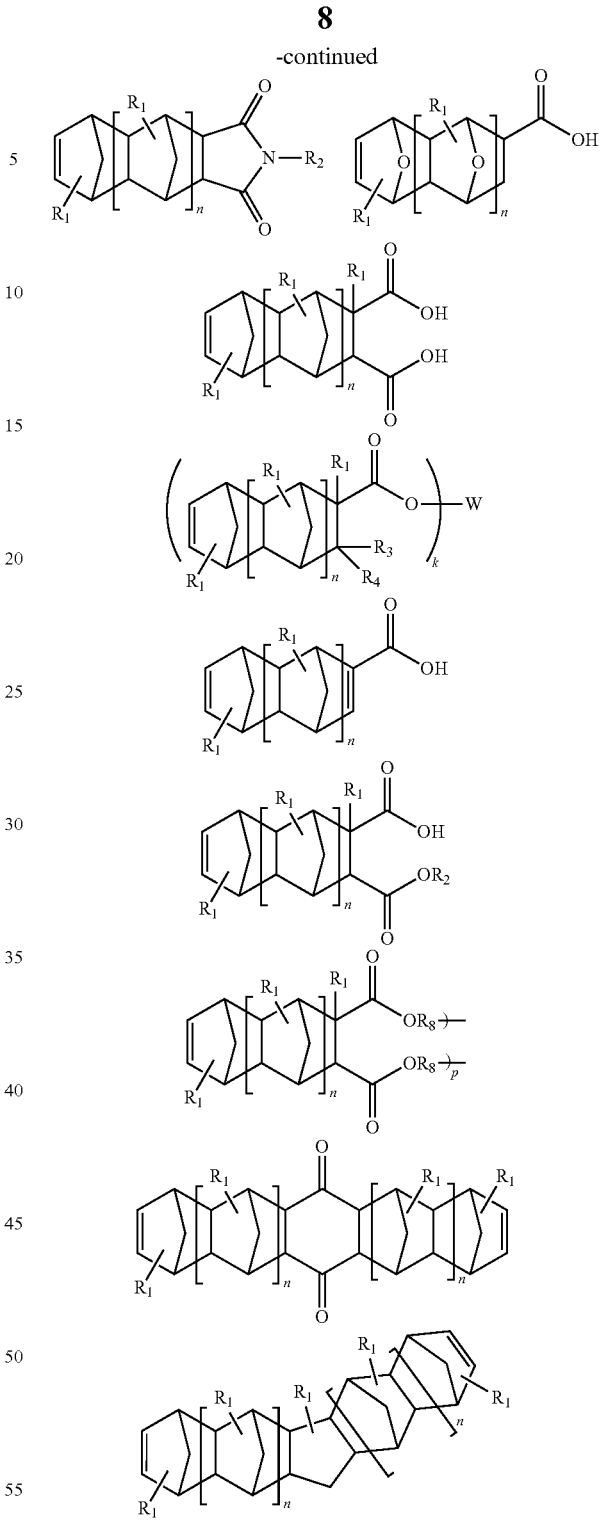

wherein the definitions of $R_{1-8}$, k, p and n are the same as those in the Formula-1, W represents a monovalent, divalent, trivalent or tetravalent connecting group selected from the group consisting of a substituted or unsubstituted alkyl or alkylene group having 1 to 100 carbon atoms.

The most preferred structure is norbornenyl acid derivative, which is prepared from Diels-Alder reaction of cyclopentadiene and unsaturated carboxylic acid or anhydride and ester such as acrylic acid, maleic anhydride or maleate, maleic half ester. The norbornenyl acid derivative contain both carboxy group and active double bond and is a very useful A-B type of cyclic monomer for production of norbornanyl polymer or oligomer in this invention.

The conditions that should be used in the Diels-Alder reaction depend upon the cyclic diene and dienophile being used. The Diels-Alder reaction of the abovementioned can be carried out by either a batch system or a continuous system with or without solvent. In a solvent-free batch system, for example, specified amounts of dicyclopentadiene and acrylic acid, maleic anhydride or ester are placed together in a reactor or in a sealed autoclave at a temperature generally ranging from about 150° C. to about 300° C., and more preferably at about 180-220° C. At these temperatures the dicyclopentadiene undergoes a reverse Diels-Alder reaction (crack or de-dimerize) to produce cyclopentadiene which reacts in situ with the dienophile and produces 4+2 adducts. The pressure may vary as needed to keep reactants in the liquid state at the temperature selected and generally will range from about 1 to 20 atmospheres. Besides being solvent-free, the described procedure allows for almost complete utilization of dicyclopentadiene and avoids production and handling of hazardous cyclopentadiene and residual polymer.

When cyclopentadiene is used as diene for synthesizing norbornenyl derivatives the reaction temperature is in the range of −20 to 50° C., preferably 10 to 20° C.

Usually the product of a Diels-Alder reaction is a mixture of isomers, including substitution position isomers as well as stereoisomers.

2: Addition of Carboxylic Acid to Norbornenyl Derivative

The functional group substituted norbornenyl derivatives prepared as above are then reacted with carboxylic acid to form the desired substituted norbornanyl esters. This acidic addition reaction is the hydrocarboxylation of norbornenyl double bond and can be illustrated by the following reaction.

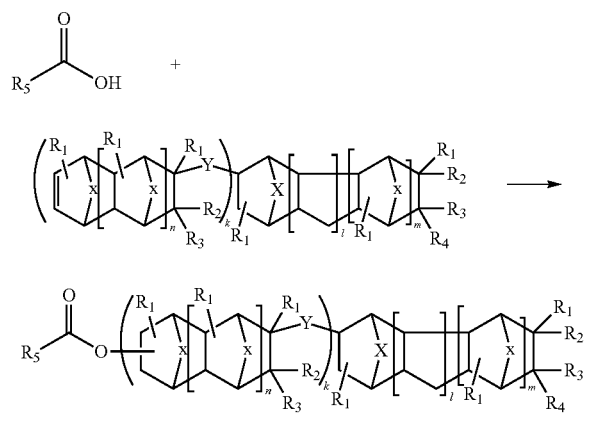

wherein the definitions of $R_{1-8}$, x, y, and k, l, m, n are the same as those in the Formula-1.

In this addition reaction, carboxylic acid insert the double bond of norbornenyl ring to form an ester group and it is a self-catalytic acid addition reaction or self-catalytic hydrocarboxylation. There are four types of hydrocarboxylation according the present invention.

1. Hydrocarboxylation of Norbornenyl Derivative with External Carboxylic Acid Shown in the Reaction Below.

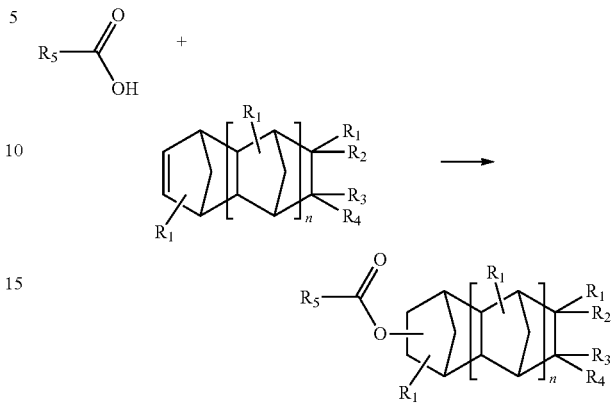

2. Intermolecular Hydrocarboxylation of Norbornenyl Acid Derivative

For carboxyl group functionalized norbornenyl derivative, which is also A-B type monomer, the intermolecular acidic addition will lead to an oligomer or polymer, which may be represented by the reaction below.

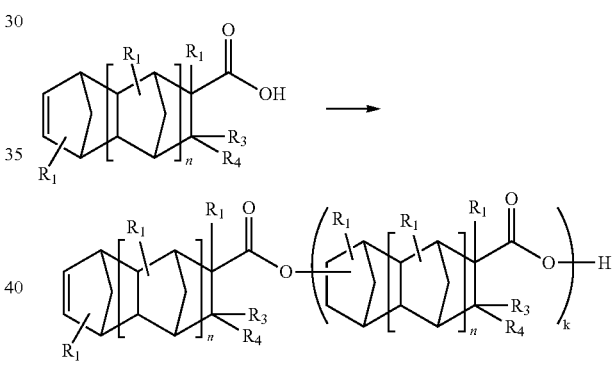

It is a self-addition self-catalytic (SASC) reaction and a useful method for carbon-carbon bond construction. In this SASC reaction the carboxyl group acts both as catalyst and nucleophile.

It is possible to prepare cyclic oligomer or polymer by SASC process with combination of different acidic norbornenyl derivatives such as shown in the following reaction.

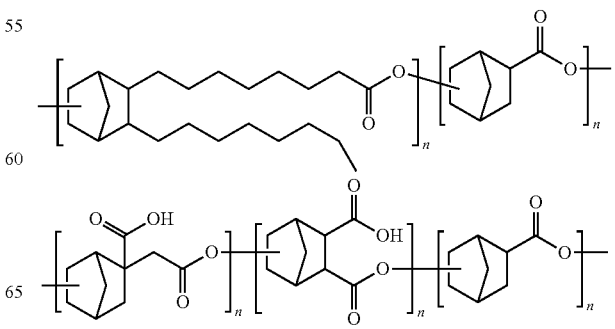

-continued

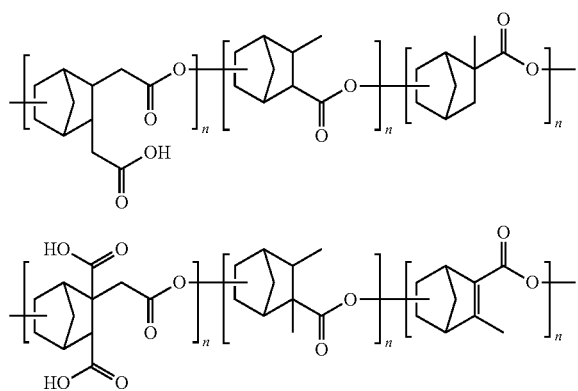

The norbornenyl oligomers prepared by the present invention can be used as raw material not only for acid addition but also acts as a cyclic olefin for some other reactions such as polymerization, hydration and epoxidation which may be represented by the following reaction.

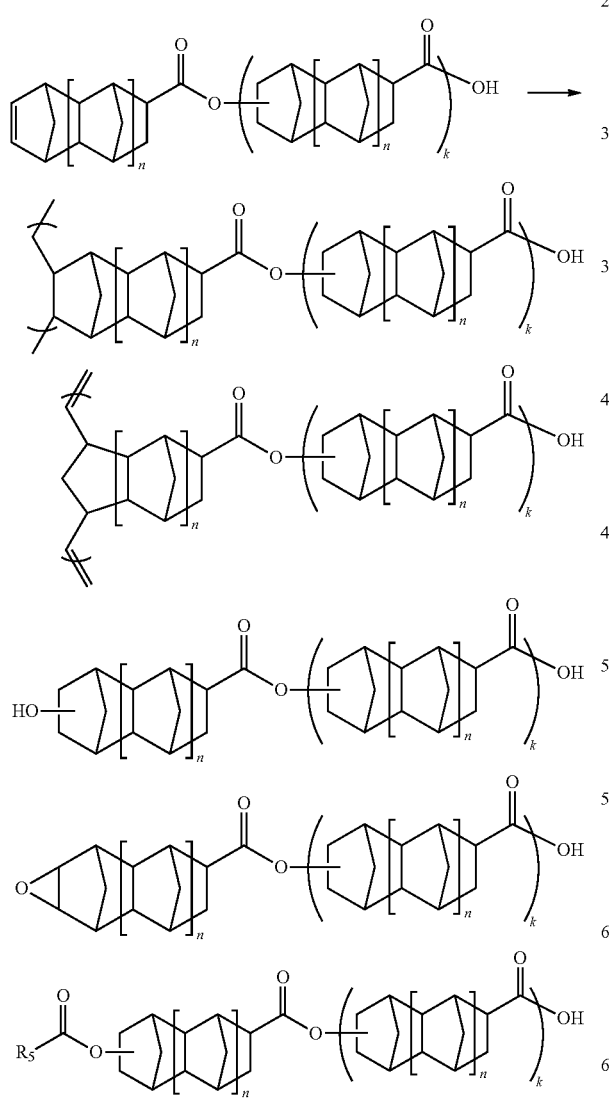

3 Combined Intermolecular Hydrocarboxylation and External Hydrocarboxylation

When a norbornenyl acid derivative reacts with external carboxylic acid, depending on reaction condition, the product may be a adduct of norbornenyl acid derivative with external carboxylic acid and/or an adduct of norbornenyl acid oligomer with external carboxylic acid. The norbornenyl acid oligomer is the product of intermolecular self-addition of norbornenyl acid derivative as illustrated in the following reaction.

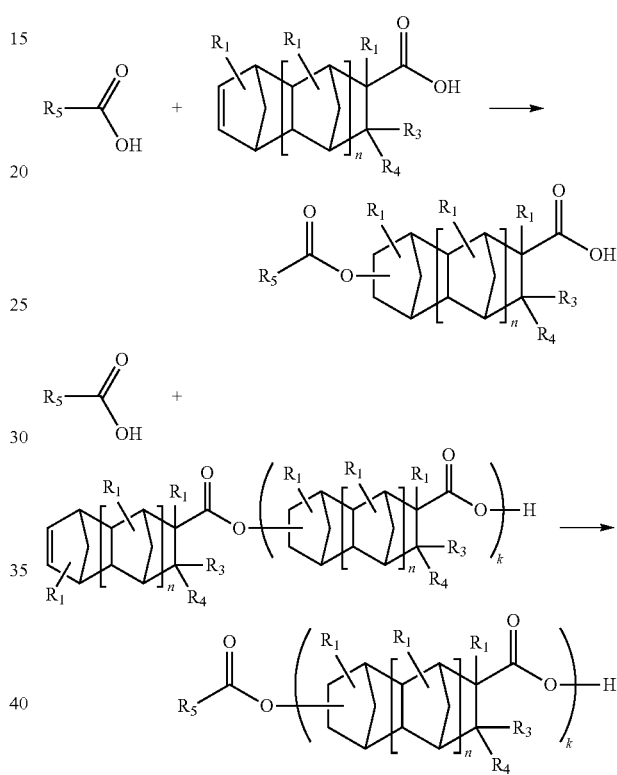

4 Intramolecular Hydrocarboxylation of Norbornenyl Acid Derivative

A norbornenyl acid derivative may undergo a self-addition to produce a norbornanyl lactone such as 2,6-norbornane carbolactone or 2,6-norbornane carbolactone-3-carboxylic acid, which is an intramolecular self-adduct of norbornenyl acid derivative. The yield of intramolecular lactonization is strongly dependent on the reaction condition such as acid activity and temperature. The other norbornenyl derivative substituted with active hydrogen may also undergo intramolecular cyclization as illustrated in the reaction below.

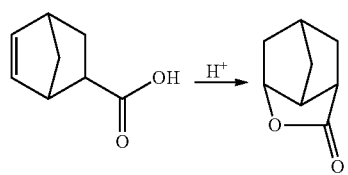

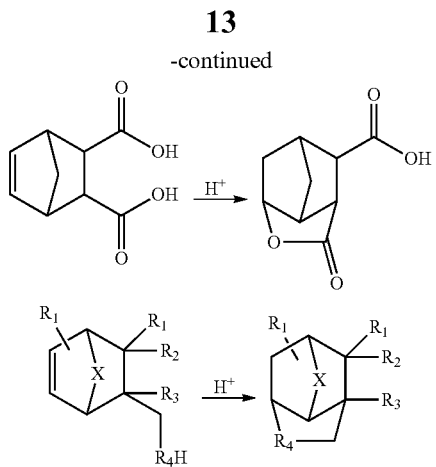

These four types of hydrocarboxylation can be controlled with different reaction formula, procedure and condition to prepare desired product. The preferable examples of norbornanyl derivatives of the present invention include as illustrated in the reaction below.

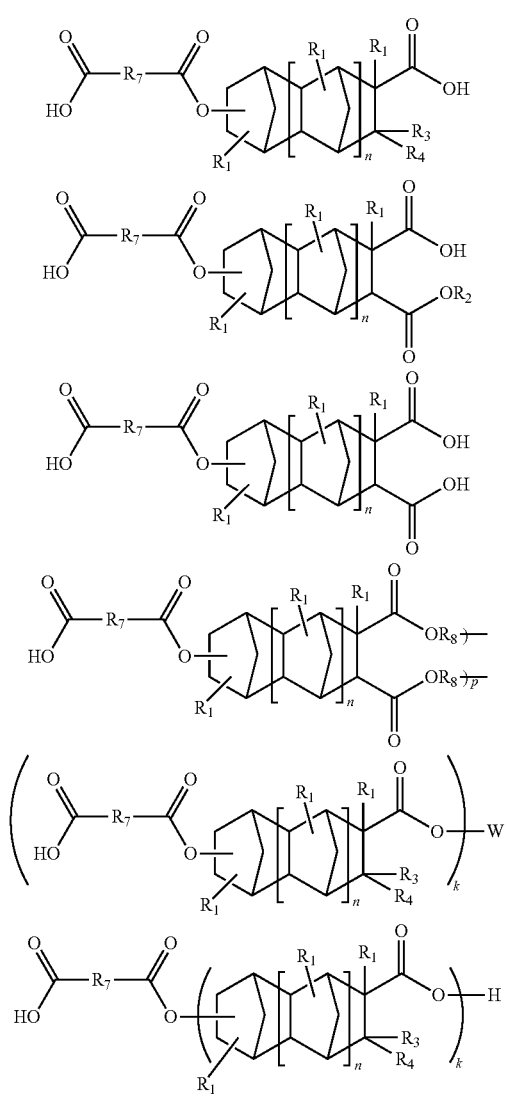

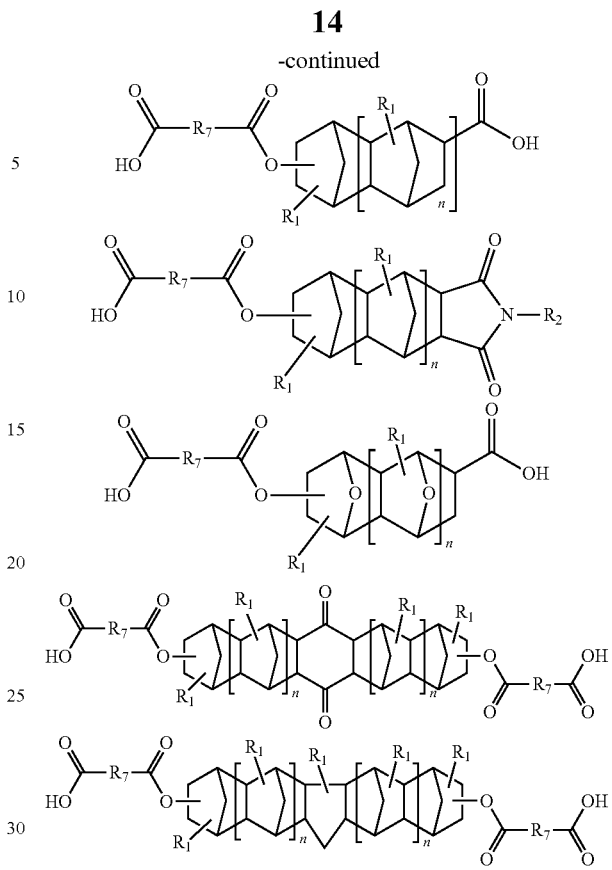

wherein the definitions of $R_{1-8}$, W and p, k, l, m, n are the same as those in the Formula-1. The carboxylic acid used for acid addition of the norbornenyl ring composition is suitably a carboxylic acid including saturated or unsaturated mono- or poly-carboxylic acids having up to about 1000 carbon atoms, preferably up to about 100 carbon atoms. Examples of suitable carboxylic acids are oxalic acid, succinic acid, succinic anhydride, glutaric acid, adipic acid, azelaic acid, sebacic acid, malic acid and other aliphatic dicarboxylic acids; 1,4-cyclohexanedicarboxylic acid, 1,3-cyclohexanedicarboxylic acid, 1,2-cyclohexanedicarboxylic acid, 2,3-norbornanedicarboxylic acid, 2,5-norbornanedicarboxylic acid, 2,6-norbornanedicarboxylic acid, perhydro-1,4:5,8-dimethanonaphthalene-2,3-dicarboxylic acid, adamantanedicarboxylic acid, 1,3-dimethyl-5,7-adamantanedicarboxylic acid, and other alicyclic dicarboxylic acids and the anhydrides of these acids; maleic acid, methyl maleic acid, fumaric acid, itaconic acid, mesaconic acid, citraconic acid, tetrahydrophthalic acid, methyl tetrahydrophthalic acid and other ethylenically unsaturated dicarboxylic acids and the anhydrides of these acids; terephthalic acid, isophthalic acid, phthalic acid, 2,6-naphthalenedicarboxylic acid, 4,4'-biphenyldicarboxylic acid, 4,4'-diphenyl ether dicarboxylic acid, 4,4'-diphenylmethanedicarboxylic acid, 4,4'-diphenyl sulfone dicarboxylic acid, 4,4'-diphenylisopropylidenedicarboxylic acid, 1,2-diphenoxyethane-4',4''-dicarboxylic acid, anthracenedicarboxylic acid, 2,5-pyridinedicarboxylic acid, diphenyl ketone dicarboxylic acid, and other aromatic dicarboxylic acids; suitable monocarboxylic acids may be mentioned the monoester of above dicarboxylic acids, such as monoester of maleic acid, monoester of fumaric acid, aromatic carboxylic acids, for instance: benzoic acid; aliphatic carboxylic acids, for instance: fatty acids having from about 8 up to about 25 carbon atoms such as oleic acid, stearic acid, palmitic acid, linoleic acid and the like; rosin acids or derivatives of rosin acids, acrylic acid, methacrylic acid, propionic acid, 2-methyl propionic acid, butyric acid, 3-methyl butyric acid, valeric acid, trimethyl propionic acid, caprylic acid, 2-ethyl caproic acid and trimethyl caproic acid; and cycloaliphatic monocarboxylic acids, for instance: hexahydrobenzoic acid and naphthenic acid, hydroxy carboxylic acid such as dimethylolpropionic acid, 3-hydroxypropionic acid, lactic acid, glycolic acid, tartaric acid, citric acid and half ester of these dicarboxylic acid. Each of these carboxylic acid components can be used alone or in combination.

Oligomers or polymers that contain acidic group may be used and therefore are capable of reacting with the norbornyl-type double bond and acting as a carboxylic acid. Furthermore, because the number of acidic groups on the polyester or acrylic polymer can be varied by changing the monomer composition, the acid addition ability of the polymer can exceed that of carboxylic acid with low molecular weight. It especially works well for synthesizing the polymers with norbornane ring or in a one-pot industry process. The use of polymers with multiple acidic groups allows the preparation of functional resins with blends of molecular weight, viscosity, solubility and softening point properties that cannot be obtained by using traditional acidic raw materials containing one or several acidic groups. For example, the use of multiple acidic group-containing polyester (a polyester with high acid number) as acid to react with a Diels-Alder adduct allows the synthesis of polyester resins containing bridged cyclic ring in a one-pot process.

Among these carboxylic acids, biobased multifunctional carboxylic acid, such as succinic acid, malonic acid, malic acid, maleic acid, maleic anhydride and fumaric acid are preferably employed, maleic acid preferably generated in situ by reaction of maleic anhydride with water.

The carboxylic acid and norbornenyl derivative can be combined in a variety of different ratios varying from stoichiometric amounts up to an excess of either reactant. More specifically, acid to norbornenyl ring molar ratios may vary from about 1:10 to 10:1 as needed or desired.

The amount of carboxylic acid compound depends on carboxyl functionality, the total number of norbornene ring of the reaction mixture and final application of the desired product.

In some cases, if norbornene derivative is substituted with hydroxyl group, the amount of carboxyl acid should be increased, because carboxyl reacts not only with double bond present in norbornenyl groups, but also with the alcoholic hydroxyl groups present in the norbornenyl compound. For norbornenyl acid derivative, which is an A-B type monomer that enables SASC polymerization, the ratio of external carboxylic acid depends on the amount of reactive norbornenyl ring which is related to degree of SASC polymerization. One advantage of the present invention is that the carboxyl functionality and molecular weight of final product can be adjusted by the degree of SASC polymerization of A-B type monomer.

The carboxylic acids and ester bond on resulting norbornanyl derivative will change their compatibility with other resins, solubility in solvent or monomer, softening points, rheological properties, and mechanic properties desirable for use in the formulation of inks, coating, adhesive etc.

When using the norbornane derivative of this invention as resin for preparing printing inks, it is especially preferred that the amount of the carboxylic acid should be 0.01 to 0.4 mol per 100 g of the norbornanyl derivative. If the amount of the carboxylic acid is smaller than 0.01 mol per 100 g of the norbornane derivative and the amount of the polar group of the resin is small, the resin will have poor dispersibility in pigments and a printing ink prepared from this resin will have poor flowability and exhibit a poor printing effect.

When using norbornane derivative of this invention as alkyd resin for preparing water dispersed coating, it is especially preferred that the amount of the carboxylic acid should be enough for neutralization of acid with amine.

For some resin applications the excess amount of carboxylic acid may be used to convert all unsaturated norbornene ring to saturated norbornane ring. The unreacted norbornene ring may lead to an ultra high molecular weight or even gelling when it is cooked at high temperature with glycol for a polyester, such as higher than 210° C. due to the Ene reaction.

When less reactive Diels-Alder adduct or weak carboxyl acid is used for hydrocarboxylation it is possible to use excess amount of acid to speed up the reaction. After reaction is finished the free acid may be removed, preferably by vacuum distillation or water extraction, to reduce the acid number to a desired level. For some norbornenyl acid derivatives the excess amount of carboxylic acid may lead to lactonization.

The functional group substituted norbornenyl derivatives obtained by the Diels-Alder reaction of cyclopentadienes and dienophile are a mixture of isomers and include the substitution position isomers as well as stereoisomers of each substitution position isomer, which makes a mixture of multi-component isomers. Furthermore, the addition of acid to norbornenyl double bond may happen at different positions and the resulting norbornanyl derivative is a complicated mixture of position isomers and stereoisomers.

These isomers have closely related boiling points and react substantially the same in the formation of the new products of the invention so they can be used as a mixture directly subjected to hydrocarboxylation without further separation.

The process conditions that should be used in the acid addition reaction depend upon the particular carboxylic acid and norbornenyl derivative used. The acid activity (pKa) of carboxylic acid, the ring strain and the substitution position on norbornene ring play an important role in this reaction.

The reaction between the carboxyl acid and norbornene double bond to form the functional group substituted norbornane can be accomplished by heating the components together in a reactor or a sealed autoclave at a temperature generally ranging from about 50° C. to about 250° C., and more preferably at about 100-220° C.

The carboxylic acid with higher acid activity reacts with norbornene double bond at lower temperature and the carboxyl acid with lower acid activity reacts with norbornene double bond at higher temperature. For example the addition reaction temperature between adipic acid (pKa 4.43) and 5-norbornene-2-carboxylic acid is in the range 140-220° C., the reaction temperature between maleic acid (pKa 1.83) or oxalic acid (pKa 1.23) and 5-norbornene-2-carboxylic acid is in the range 70-130° C. In industry maleic anhydride and water are used to produce maleic acid in situ. The anhydride hydrolysis and acid addition reaction substantially occur after the formation of maleic acid. Since both reactions are exothermic, it is necessary to control the temperature by proper cooling. At elevated temperature, such as above 130° C. maleic acid will isomerize to fumaric acid (pKa 3.03), which is less reactive acid and a higher temperature, such as 150-200° C. is needed to finish the insertion reaction across a norbornenyl double bond site. Generally the product is the half-ester mixture of maleate and fumarate. The ratio of these two isomers is dependent on the reaction condition including temperature and catalyst.

The addition reaction of dicyclopentadiene with maleic acid is known. See for example U.S. Pat. Nos. 6,515,071 and 5,252,682, typically the reaction is carried out at a temperature range of 100-130° C., which is high enough to ensure that the dicyclopentadiene reacts with the acid (about 100° C.) but not high enough to cause the dicyclopentadiene to decompose (about 150° C.). Compared with dicyclopentadiene the norbornenyl derivatives are more stable. For example 5-norbornene-2-carboxylic acid having a boiling point about 260° C. can react with adipic acid in 100-230° C. while dicyclopentadiene starts to decompose at about 150° C. Some weak acids, which can not react with dicyclopentadiene, can react with norbornenyl carboxylic acid at higher temperature. Another advantage in this novel process is that the addition of acid to double bond of norbornenyl ring prevents the reverse Diels-Alder reaction.

The reaction temperature and time are also related to the molecular weight of reagents, lower temperatures and shorter times are used for the reaction of carboxylic acids or norbornenyl derivative having lower molecular weight. The higher temperatures and longer times are used for the reaction of carboxylic acids or norbornenyl derivative having higher molecular weight.

The Diels-Alder reaction and acid addition reaction of the resulting norbornenyl derivative can be carried out by a multi-step one-pot process. In a one pot-process, for example, specified amounts of dicyclopentadiene and acrylic acid are placed together in a reactor or in a sealed autoclave at a temperature generally ranging from about 150° C. to about 220° C. The pressure may vary as needed to keep reactants in the liquid state at the temperature selected and generally will range from about 1 to about 20 atmospheres. Cyclopentadiene, formed in situ, reacts with the acrylic in a thermodynamically controlled reaction to form Diels-Alder adduct. Adipic acid is charged and heated at about 170° C. to about 210° C. to produce a saturated norbornanyl dicarboxylic acid which may be packaged for marketing or subjected next reaction such as polycondensition with glycol for a polyester product.

Solvents such as toluene may be utilized to prevent coagulation of materials or reaction products, but in many cases the cyclic diene or dienophile furnishes sufficient fluidity for the desired addition reaction and the viscosity of the product is low in the reaction temperature. For a manufacturing solvent-free one-pot process, it is preferred to use diene, dienophile, dicarboxylic acid or glycol to work as both reagent and solvent.

The reaction should occur under inert condition by purging with nitrogen. The reaction may be accelerated by using acidic catalysts, for instance sulphuric acid, phosphoric acid, triflic acid, borium trifluoride or complex compounds thereof; the use of a catalyst, however, is not absolutely necessary. A thermal-polymerization preventing agent, such as hydroquinone and 4-methoxyphenol, can be added to the reaction system.

It is convenient to check the progress of converting norbornenyl derivative to norbornanyl derivative by testing the acid number in the present invention. The drop in acid number of the products indicates the consumption of the carboxylic acid. This results from the addition of carboxyl group across double bonds on norbornene ring to produce norbornane esters. The norbornanyl ester derivative composition according to the present invention suitably has an acid number 1-500, more preferably about 10-250, and with molecular weight from 100-10000, more preferably about 200-2000.

After the completion of the reaction, the obtained norbornanyl ester derivative can be utilized directly as the binder for ink and coating as is, or the reaction product can be recovered by removing volatile materials such as the unreacted materials, low boiling substances, and the solvent when employed. It may also be purified by any suitable means, if necessary. For example, after the reaction is completed, water and an organic solvent such as toluene can be added to the resulting reaction mixture, the reaction product is extracted into the oil layer and isolated from the reaction mixture, after which the oil layer containing the reaction product is washed, isolated and concentrated under reduced pressure to obtain a purified product. Furthermore, if necessary, the resulting product can be subjected to vacuum distillation or crystallization purification to obtain a further purified product. The physical state of the product can be solid or liquid at ambient temperature depending largely on the types of reactants used. The reaction product may suitably be blended with solvent or diluents, other resins, additive, such as stabilizer, pigment before packaging. The viscosity and the concentration of binders are controlled to provide the resin suitable for ink or coating application. For a one-pot process, the resulting norbornanyl derivative will be directly subjected to the next reaction for polymer production.

The carboxyl acid substituted norbornenyl derivative molecule possesses two chemically reactive centers, the double bonds and the carboxyl group. Many modifications in structure and numerous derivatives are obtainable from the two functional groups. For example acid addition of maleic acid with 5-norbornene-2-carboxylic acid will lead to an unsaturated dicarboxylic acid with a molecular weight 254 and an acid number of 442 mg KOH/g. If 5-norbornene-2-carboxylic acid is heated for oligomerization, the acid addition of maleic acid with this oligomer will lead to an unsaturated dicarboxylic acid with a higher molecular weight and a lower acid number. In this way it is possible to design and synthesize cyclic dicarboxylic acid with different acid number. The acid addition of modified and unmodified Diels-Alder adduct can be illustrated by the reaction below.

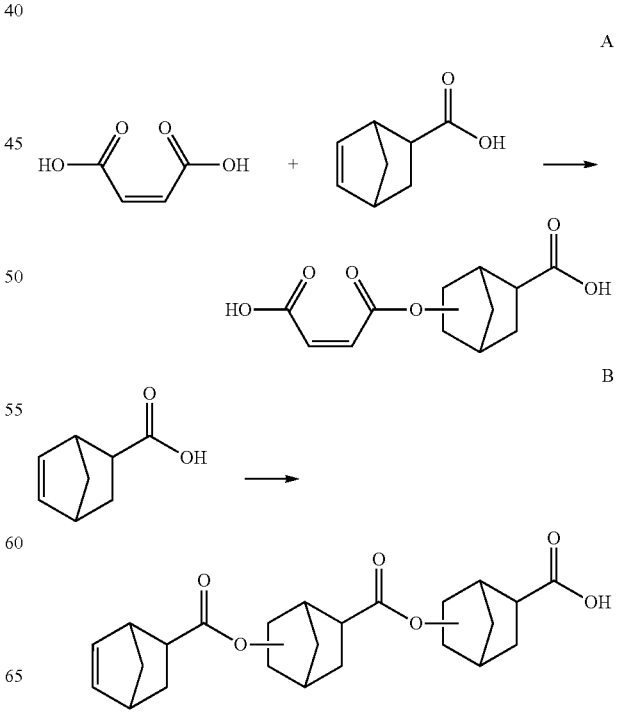

19

-continued

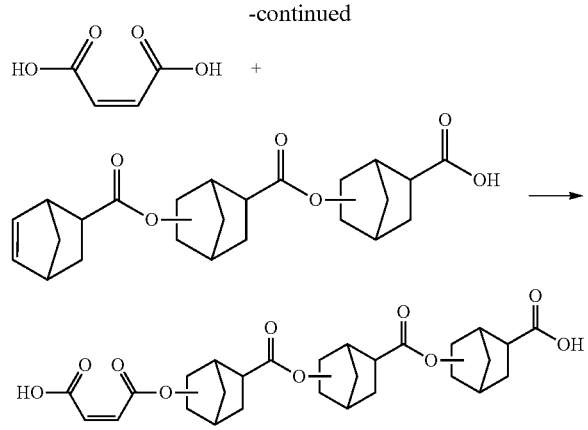

20

In the present invention the maleic acid monoester (maleic acid half ester) is a versatile dienophile, which is easily prepared from reaction of maleic anhydride with monohydric or multihydric compound or from the addition of maleic acid with unsaturated double bond. One method used in this invention is that maleic acid is used to insert the double bond of Diels-Alder adduct to produce norbornanyl maleic acid half ester, the resulting half ester is subjected Diels-Alder reaction with a diene to produce a new Diels-Alder adduct, which may be subjected to acid addition again with another maleic acid to produce a even new maleic acid half ester. This process is called "Double Addition Recycle" (DAR) process, which means Diels-Alder addition and unsaturated acid addition is repeatedly used until a desired norbornanyl polyacid is obtained. DAR process can be represented by the following reaction.

A

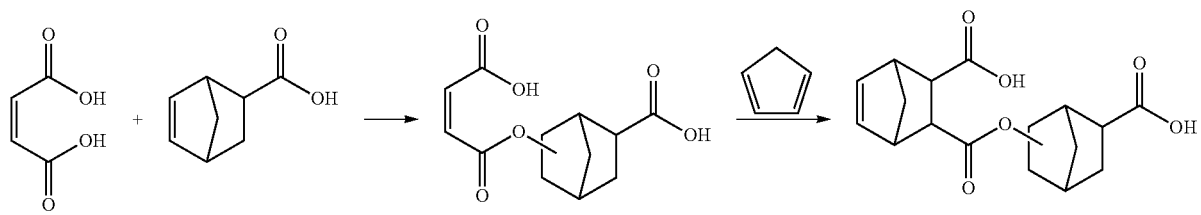

B

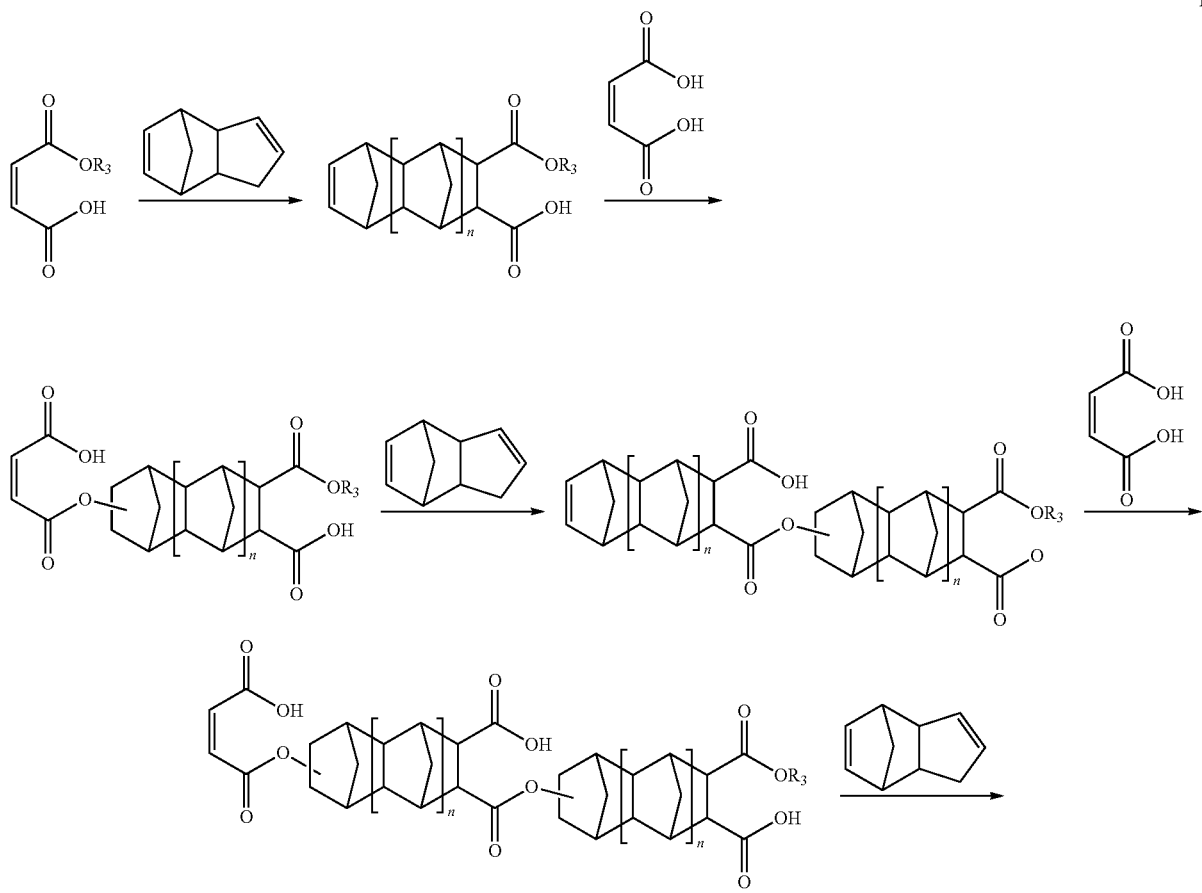

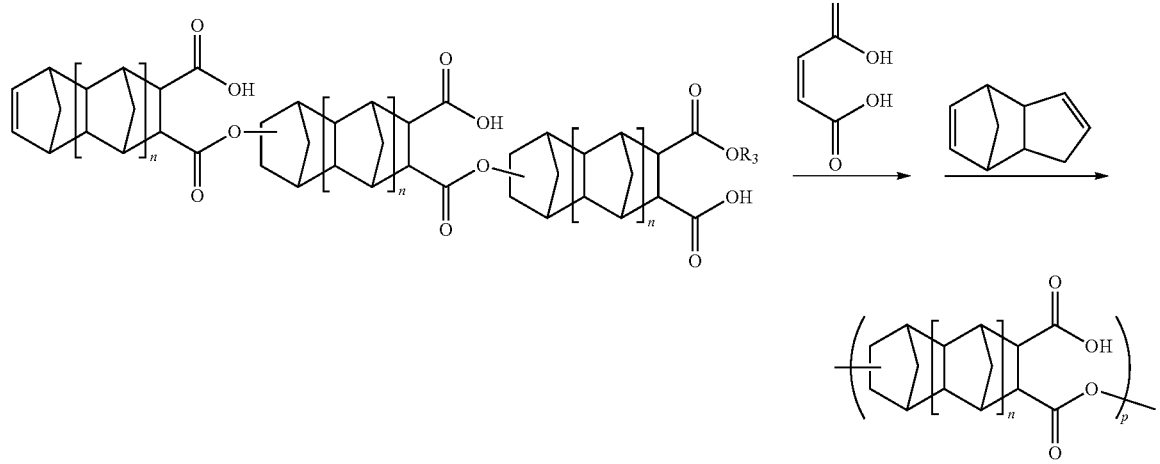

The preferred monohydric compounds include dicyclopentadiene alcohol, 2-ethyl-1-hexanol, methylcyclohexanol and adamantanol etc.

It is also possible to prepare a norbornanyl polyester from dicyclopentadiene and maleic acid in a one-pot process. For example one mole of maleic acid is heated with two moles of dicyclopentadiene to form a norbornenyl dicarboxylic acid half ester, which undergoes an intermolecular acid addition to form a norbornanyl oligomer as illustrated in the following reaction. It is an economic method to produce DCPD-Maleic acid based oligomer or polymer which is useful in ink and adhesive application.

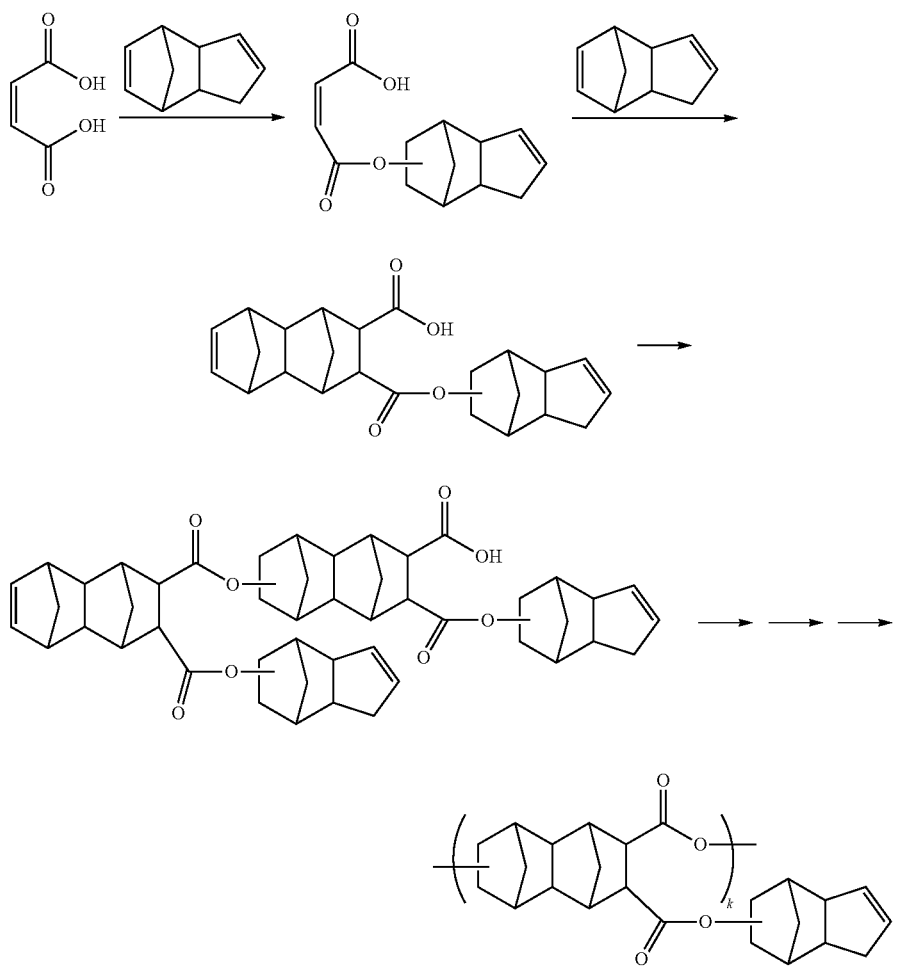

Diels-Alder adduct or norbornenyl derivative itself, which is prepared from diene and dienophile, can be used as dienophile. As a dienophile, the reactivity of the norbornenyl derivative is determined by its substituted group on the ring and molecular weight.

The carboxy group exerts a great influence upon the reactivity of the norbornenyl ring double bond. The carboxylic group of maleic half ester favors cyclopentadiene addition to form a norbornenyl acid derivative. The carboxy group of norbornenyl derivative favors acid addition to form a norbornanyl derivative.

One of the special properties of the norbornenyl derivative containing an active hydrogen such as carboxyl or hydroxyl is its two reaction selectivities. The active hydrogen may attack the double bond of another norbornenyl molecule to form a polymer acting as an A-B type monomer, but it may also attack double bond of its own molecule to form a cyclization product. For a norbornene derivatives substituted with carboxyl group it may not only to be polymerized to a polymer but also possible to subject an intramolecular self acid addition reaction. Usually this lactonization happens with strong acid as catalyst and the unsaturated norbornene ring is converted to a lactone ring structure according to the following reactions.

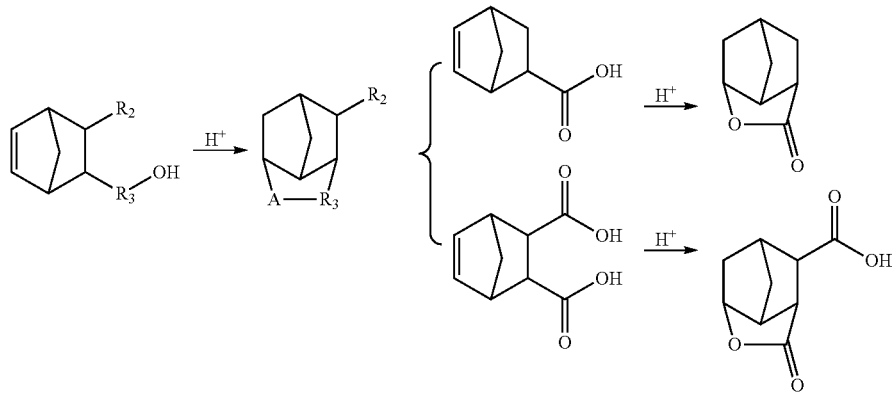

The formation of the lactone is dependent on the acidity of the acid catalyst and the structure of the norbornenyl derivative. Higher acidity favors the cyclization. It is possible to control the reaction selectivity for an intermolecular addition to produce a polymer or for an intramolecular addition to produce a lactone. It was found that in the addition reaction of maleic acid to norbornene carboxylic acid, the product contains 2,6-norbornane carbolactone-3-carboxylic acid, which is produced from intramolecular self addition. The excess amount of maleic acid, longer reaction time and higher reaction temperature will lead to higher ratio of lactone by-product. Based on this discovery, this kind of norbornanyl lactone derivative and polymer should be prepared with a new synthetic route by using excess amount of maleic acid as acid catalyst.

The lactone acid is a useful chemical raw material, which possesses both polarity attributable to the lactone structure and rigidity attributable to the fused tricyclic ring. A lactone-containing polymer possesses a well-balanced profile of etching resistance and substrate adhesion, and it may be used for resist composition in precise microfabrication.

The lactone acid can be synthetically prepared as described in U.S. Pat. No. 6,517,994. The starting compound, e.g., 5-norbornene-2,3-dicarboxylic acid anhydride is dissolved in water and the solution is heated in the presence of a strong acid catalyst to form the norbornyl carboxylic acid compound with lactone ring structure. The acid catalyst used in the above mentioned lactone ring-forming reaction includes inorganic acids such as sulfuric acid, nitric acid and hydrochloric acid; organic acids such as trifluoroacetic acid, p-toluenesulfonic acid and methanesulfonic acid and cation-exchange resins.

Another objective of this invention is to develop a new synthesis method for a polyester containing lactone structure. It was found that maleic acid can be used as both catalyst and reactant for production of lactone polyester in a SCSA one-pot process as represented by the following reaction.

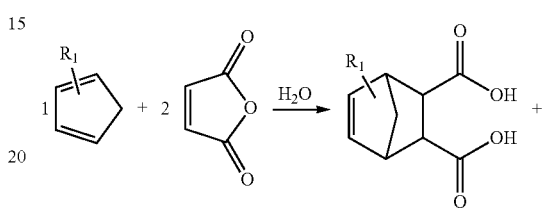

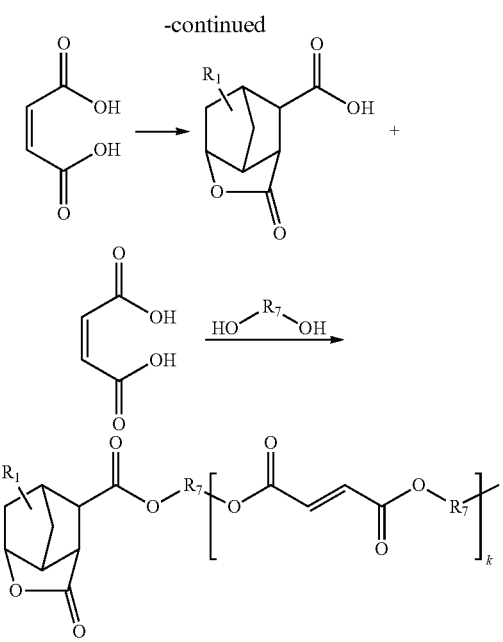

The reaction is conducted by reacting cyclopentadiene with excess of maleic acid in water under agitation in an atmosphere of nitrogen. After completion of the Diels-Alder reaction, the reaction mixture, which includes 5-norbornene-2,3-dicarboxylic acid and free maleic acid, is heated in 80 to 130° C. for lactonization. When there is no 5-norbornene-2,3-dicarboxylic acid as detected by gas chromatographic analysis, the reaction is stopped and ready for separation of lactone acid or directly go to polyester synthesis with glycol in next step. The advantage of this new method is avoid the use sulfuric acid catalyst. While it is possible to get pure lactone acid by a conventional work-up treatment such as recrystallization, purification is not necessary for the production of polyester, which is based on both maleic acid and lactone acid as raw material. It was also found that it is possible to react oxalic acid with nadic anhydride in water to produce lactone acid.

Maleimide and its derivatives are prepared from maleic anhydride by treatment with amine followed by dehydration. A special feature of the reactivity of maleimides is their susceptibility to additions across the double bond through Diels-Alder reaction. In this invention, maleimide is used as a dienophile and reacted with diene to form a nadimide.

N-substituted maleimide can be derived from a primary monoamine, a primary diamine or a primary triamine. Exemplary monovalent primary amines include stearyl amine, cyclohexylamine, cyclopentylamine, methylamine, ethylamine, propylamine, butylamine, pentylamine, hexylamine, octylamine, decylamine, dodecylamine, tetradecylamine, hexadecylamine, octadecylamine, oleylamine, ethanolamine, n-propanolamine, i-propanolamine, butanolamine, etc.

Exemplary primary diamines contemplated for use herein include diamines such as: ethylenediamine; hexamethylenediamine; isophoronediamine; methylenediamine; methylenedi(cyclohexylamine); 2-methyl-1,5-pentanediamine; trimethyl-1,6-hexanediamine, etc.

The synthesis of Diels-Alder adduct of maleimide is typically accomplished in three steps. The first step involves the generation of an N-substituted maleamic acid by the direct reaction of a primary amine and maleic anhydride. The second step is the cyclodehydration of the maleamic acid to form the maleimide functional group. The third step is Diels-Alder reaction of the resulting maleimide with cyclic diene. The resulting nadimide derivative will subject an acid addition with carboxylic acid to produce a norbornanyl imide derivative. The overall reaction is shown in the following reaction.

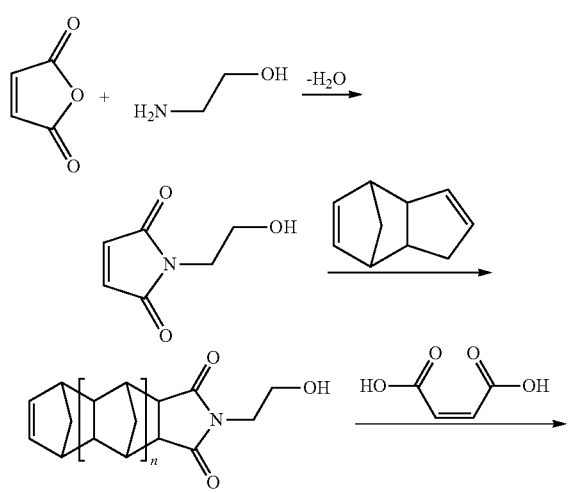

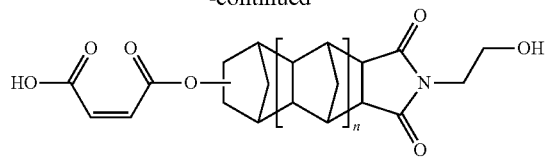

In a typical synthesis process the amine is slowly added to a solution containing a maleic anhydride to form an N-substituted maleamic acid. To avoid the potential Michael addition of the amine across the carbon-carbon double bond of the maleamic acid, a stoichiometric excess of maleic anhydride is used.

In a typical thermal cyclodehydration process an azeotropic solvent is used to permit the efficient removal of the water co-product as it forms. Suitable azeotropic solvents include cyclohexane, benzene, toluene, etc. In accordance with the present invention, it has been discovered that dicyclopentadiene is considered to be the most desirable azeotropic solvents, at same time it is also most desirable reagent for Diels-Alder reaction.

After the cyclodehydration step the resulting maleimide undergoes Diels-Alder reaction with the cyclopentadiene from dicyclopentadiene in temperature of 150-180° C. to produce a nadimide derivative, which is reacted with dicarboxylic acid to form a functional norbornanyl imide.

Norborneneyl derivative not only reacts with carboxylic acid for a hydrocarboxylation to produce a norbornanyl ester compound but also reacts with hydroxyl compound for a hydroalkoxylation to produce a norbornanyl ether compound. The hydroalkoxylation reaction may be represented by the following reaction:

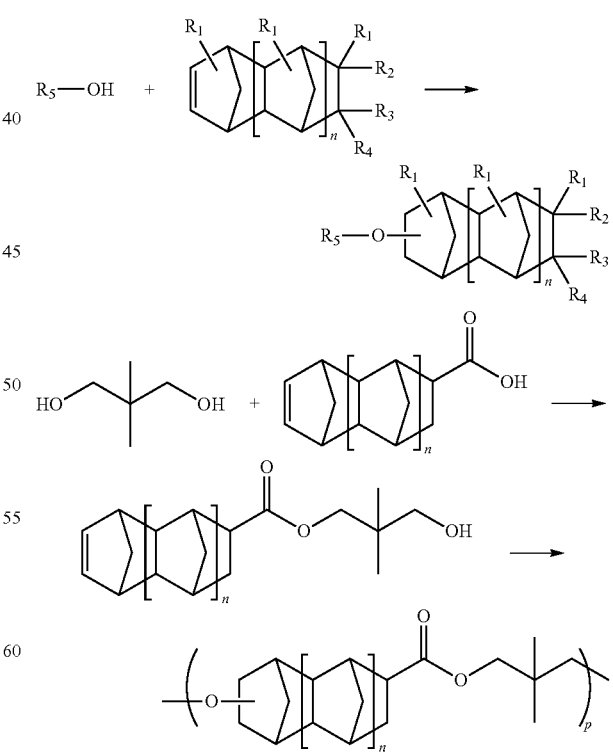

wherein the definitions of $R_{1-8}$, p and n are the same as those in the Formula-2

The norbornenyl derivatives are also capable of the hydroalkoxylation reaction. The hydroalkoxylation of norbornenyl derivative with glycol such as neopentyl glycol need a higher temperature and longer time to finish. It is possible to prepare polyetherester polyol with this chemistry.

3: Polymerization of Functional Norbornanyl Ester Derivative

The third step reaction to follow the above described the second step reaction is an esterification reaction in which the norbornanyl carboxylic acid compound obtained in the second step reaction is reacted with a hydroxyl, epoxyl or other reactive compound to form the desired functional polymer. This reaction can be illustrated by the following reaction:

hol. The molecular weight of the product increases, or depending upon the conditions, the product may become insoluble in an organic solvent or gelled.

It may be necessary to add some other carboxylic acid, acid anhydride or diester to adjust the structure. Examples of acid, anhydrides and diester suitable in the above reaction are dimethyl terephthalate, isophthalic acid, phthalic anhydride, succinic anhydride, maleic anhydride, hexahydrophthalic anhydride, tetrahydrophthalic anhydride, trimellitic anhydride, adipic acid, benzoic acid, fatty acid, 2-ethylhexanoic acid, and rosin acid.

The polyester composition comprises at least 5% by weight of the norbornanyl derivative, preferably at least 10 weight %, most preferably at least 25 weight %.

The polyester of the present invention is readily prepared by thermally reacting the above ingredients simultaneously

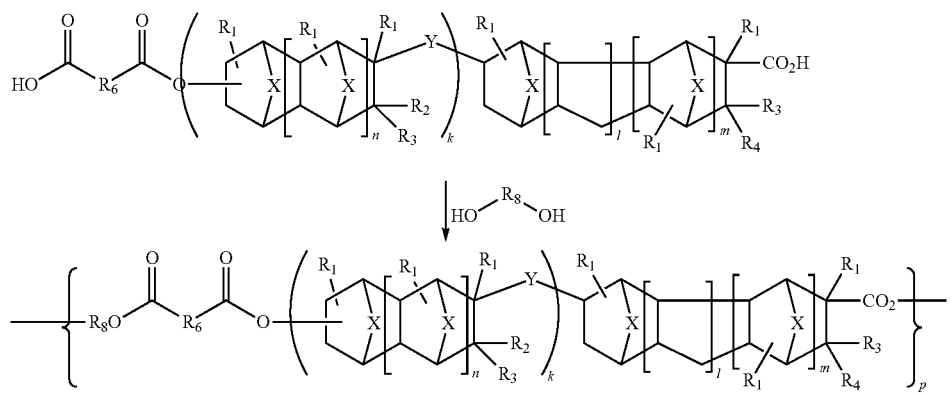

The reaction is carried out usually by mixing the starting norbornyl carboxylic acid compound with glycol such as ethylene glycol, the reactant is reacted by heating to remove water.

When multicarboxylic acid substituted norborane derivative is esterified with one or more hydroxy and/or epoxy compounds, an ester oligomer or polyester is formed. Depending on the application the polyester may have different molecular weight and chain end group.

The suitable hydroxy and/or epoxy compounds include monovalent alcohols such as propanol, isopropanol, butanol, nonanol, cyclohexanol, benzyl alcohol; divalent alcohols such as ethylene glycol, propylene glycol, 2,2-dimethyl-1,3-propane diol, 2-methyl-2-phenyl-1,3-propane diol, diethylene glycol, cyclohexane diol, 1,2-bis-hydroxymethyl-cyclohexane, 1,4-bis-hydroxymethyl-cyclohexane, 2,2-bis-(4-hydroxycyclohexyl)-propane, 1,1-isopropylidene bis (paraphenylene-oxy)di-ethanol, 1,1-isopropylidene-bis (paraphenylene-oxy)di-2-propanol; polyvalent alcohols containing three or more hydroxyl groups per molecule such as glycerol, trimethylol propane, trimethylol ethane, 1,2,6-hexane triol, pentaerythitol, di- and polypentaerythritol, sorbitol, inositol, epoxy compounds such as ethylene oxide, propylene oxide, glycidol, epoxy butane, epoxy alkyl esters of aliphatic, aromatic and cycloaliphatic monocarboxylic acids, glycidyl acrylate, glycidyl methacrylate and epoxy resins.

The amount of polyol or monovalent alcohol compound depends on the carboxyl functionality and the total number of carboxyl groups of the acidic norbornane mixture, and it is generally between 0.1 and 10.0 moles per mole of acidic norbornane compound.

When a polyhydric alcohol is used, polyester-forming reaction takes place between two or more molecules of the acid group of norbornane derivative and the polyhydric alcohol.

or in consecutive stages at a temperature of 50-300° C., preferably 80-220° C. The reaction may be carried out in the presence of an organic solvent and catalyst or in the absence of the solvent and catalyst. The water formed in the esterification reaction may be removed in the known way, and is generally done by purging with nitrogen or azeotropic distillation with the use of organic solvents such as toluene or xylene.

The progress of polycondensation may be monitored with acid number test. Depending on the final application the acid number of the cyclic polyester may be in the range 0-200 mg KOH/g. For the triglycidyl isocyanurate (TGIC) powder coating the acid number should be from 10-150 mg KOH/g. For the alkyd or thermoset plastic applications, the acid number suitably from about 5 up to about 50 mg KOH/g. To be used as polyester polyol for polyurethane formulation the polyester should contain no or very little carboxylic acid group, with an acid number 10 mg KOH/g or less.

The polyester obtained by the above method may have a softening point of 30-150° C. When the polyester is desired to be used for preparing printing ink the softening point should be 100-130° C. If the softening point is lower than 100° C., the resulting printing ink causes frequent misting and suffers from an extreme reduction in drying speed, and blocking tends to occur.

The weight average molecular weight of the resulting polyester is in the range of from about 300 up to about 500000. For fiber and plastic applications, this should from about 30000 up to about 300000 and for coating and thermoset plastic applications suitably from about 500 up to about 50000.

For powder coating application the curable polyester should have a glass transition temperature of from 40 to 100° C. and has a number average molecular weight of from 1,000 to 30,000. If the glass transition temperature or molecular weight is too lower the powder particles may melt-adhere together at room temperature. If the glass transition temperature or molecular weight is too high the melt viscosity increases and it becomes difficult to obtain a film with a homogeneous composition and smooth appearance.

DCPD, maleic anhydride and glycol based unsaturated polyester resins are well known in industry. DCPD is incorporated into unsaturated polyester resins by two different methods. One method is the acid addition reaction of maleic acid to DCPD to form a DCPD maleic half ester, which is reacted with glycol to form a DCPD terminated unsaturated polyester resin (see below). Another method is Diels-Alder reaction of dicyclopentadiene with an unsaturated polyester containing maleate/fumarate unit in chain to form a norbornene ring structure or "nadic" structure (see below), which is an abbreviation of "norbornene dicarboxylic". Both of these two kinds of resin contain unsaturated cyclic ring and are not suitable for UV resistance application. According this invention the unsaturated norbornene or nadic ring is reacted with extra maleic acid, fumaric acid, and other dicarboxylic acid or their monoester to form a saturated norbornanyl ring as shown in following reaction below.

A typical DCPD terminated unsaturated polyester:

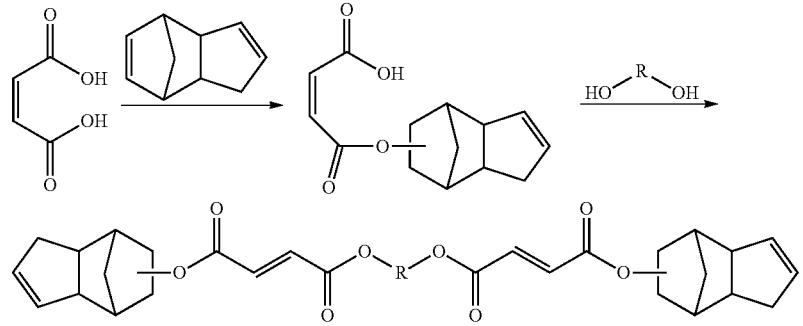

A typical nadic unsaturated polyester:

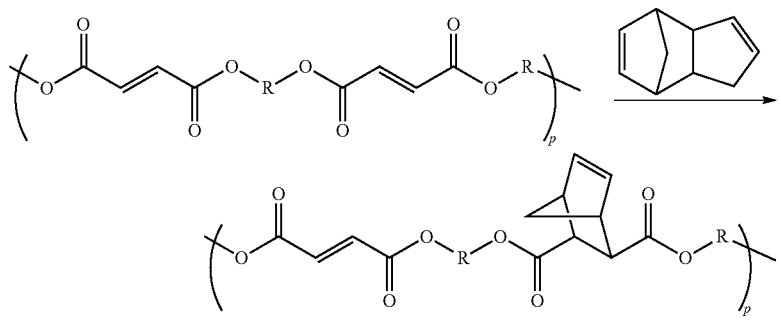

Norbornanyl unsaturated polyester by this invention:

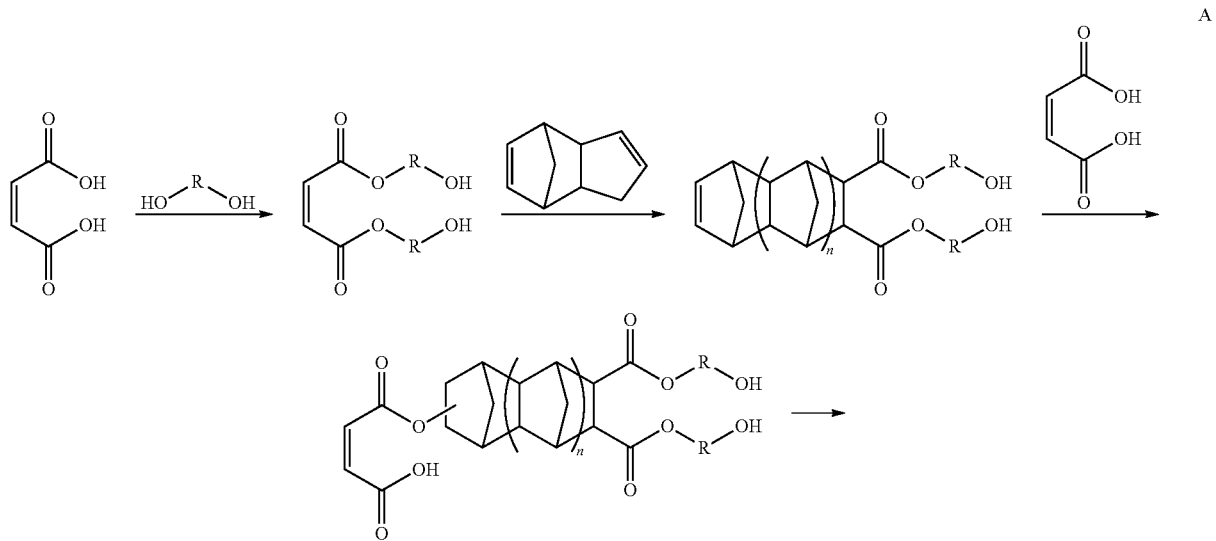

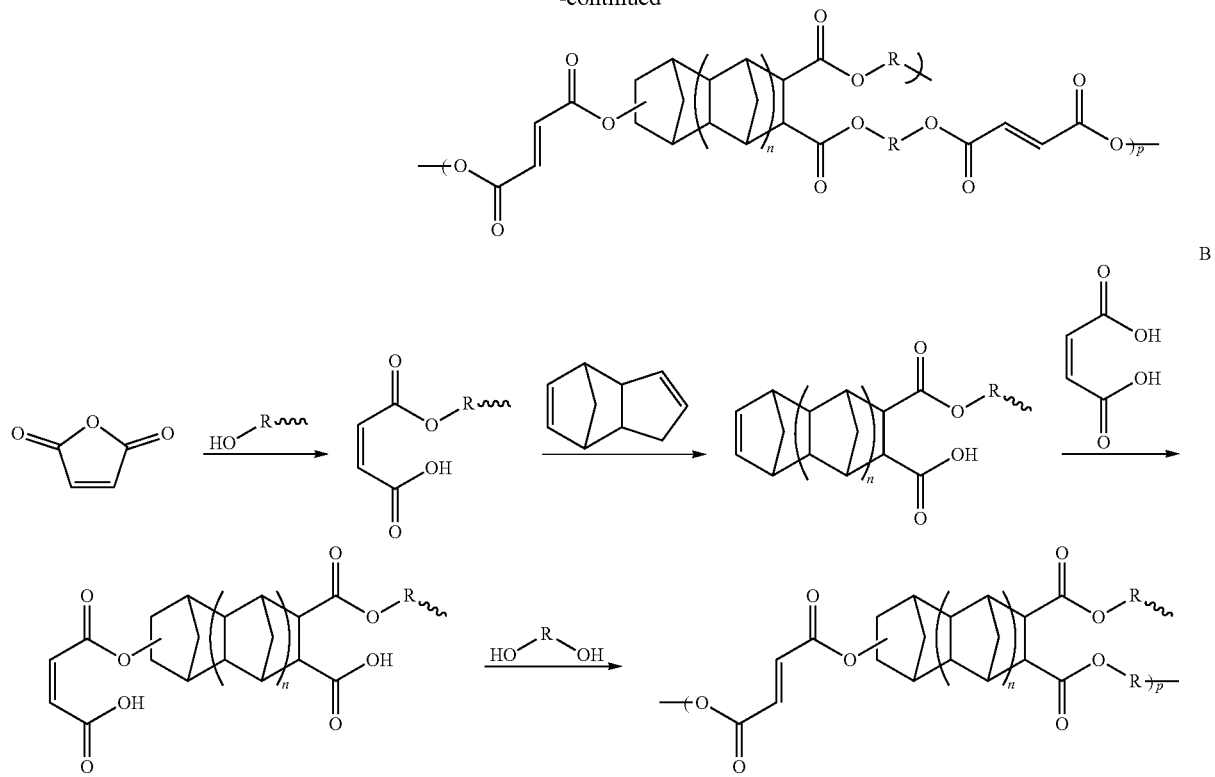

The unsaturated polyester contains an aliphatic bicyclic group, which is also an adhesion promoting functional group, and is suitable for a coating resin, specially for coil coating. This norbornanyl polyester coil coating can be cured by heating in an oven at 200-300° C.

The present invention also relates to the ester compound for plasticizers, which is used in polymers to create desired physical characteristics such as increasing flexibility and plasticity. The most popular plasticizers are phthalates such as di(2-ethylhexyl)phthalate (DEHP), di-isononyl phthalate (DINP), which have long been used for polyvinyl chloride (PVC) and other polymers. Now the use of phthalates is restricted due to environmental and health concern, and alternative non-aromatic plasticizers are needed.

According to the present invention, it is possible to produce the new generation of safe non-aromatic, non-phthalate plasticizers with cyclic acidic norbornane compounds for PVC and other polymers. The esterification of acidic norbornane compound provided by this invention with alkyl substituted monovalent alcohols such as 2-ethyl-1 hexanol will form an alkyl substituted norbornane ester with the similar structure like alkyl phthalates.

In accordance with this invention a cyclic functional polymer can be prepared with acidic norbornane compounds. The chain end group of this norbornane based cyclic polyester may be hydroxyl group, carboxyl group, epoxy, amine, isocyanate, acrylate or other functional group.

When excess amount of glycol is used it is possible to prepare a hydroxyl group end capped polyester polyol (see below) and the extra glycol can be separated out for recycling. Even further start from resulting cyclic polyester polyol it is possible to prepare reactive acrylic polyester by esterification with (meth)acrylic acid, to prepare polyurethane by reaction with polyisocyanate, to be modified with caprolactone or dimethyl carbonate etc. The aromatic ring-containing polyester resin has a drawback in that when it is subjected UV radiation it will degrade and lose gloss. The non-aromatic polyester coating will offer better UV resistance and higher gloss retention.

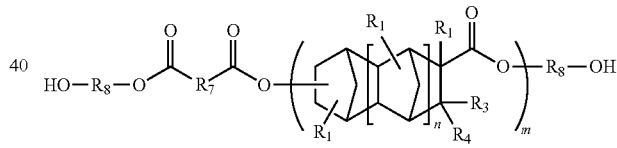

Saturated polyester polyol can be crosslinked with polyisocyanate and unsaturated polyester polyol is curable by both polyisocyanate and free radical initiator to form a hybrid thermoset plastic.

It is also possible to react these polyester polyols with excess amount diisocyanate to prepare an isocyanate functional polyester, which may undergo modification with hydroxyalkyl (meth)acrylate or other reactive compounds.

It is possible to obtain a polyester polyol by reaction of norbornane acid with epoxy compound, such as ethylene oxide, propylene oxide. The similar polyol may also be prepared by reacting with cyclic alkylene carbonates such as ethylene carbonate, 1,2-propylene carbonate, and 1,2-butylene carbonate, mixture thereof and the like.

It is possible to prepare a multi-functional polyester with curable group by esterification with unsaturated epoxy compound such as glycidyl acrylate, glycidyl methacrylate or a hydroxyalkyl (meth)acrylate such as hydroxyethyl acrylate, hydroxyethyl methacrylate. The resulting acrylic polyester (see below) can be crosslinked by thermal cure, UV cure, radiation cure, free radical cure or dual cure (thermal/UV, or UV/thermal curing) for coatings and other types of application. The incorporated bulky bridged ring structure will enhance coating performance.

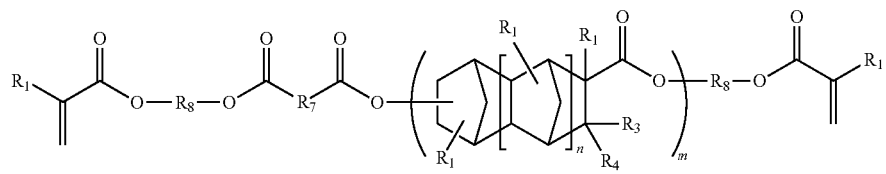

When excess amount of multifunctional epoxy compound, such as 3,4-Epoxycyclohexylmethyl-3,4-epoxycyclohexanecarboxylate (ERL 4221) is used, it is possible to prepare an epoxy group end capped polyester (see below). Furthermore starting from resulting cyclic polyester epoxy it is possible to prepare reactive acrylic polyester by esterification with (meth)acrylic acid and to prepare thermoset plastic by reacting with amine or anhydride.

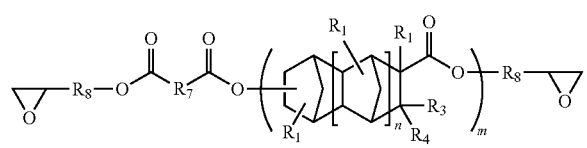

The properties of thermoset plastics are related to the crosslinking density, which depends on the ratio of reactive group such as hydroxyl group, carboxyl group or unsaturated double bond. To reach a suitable crosslinking density, the reactive polyester with a hydroxyl group at the terminal should have a hydroxyl group value in a range of from 20 to 120 mg KOH/g and the reactive polyester resin with a carboxyl group at the terminal should have an acid value in a range of from 10 to 100 mg KOH/g.

According to this invention, the norbornanyl derivatives containing maleate or fumarate groups can produce a novel polyaspartate by reacting with primary amine such as ethylene diamine and isophorone diamine. The reaction is the addition of primary amines to the activated C—C double bond in vinyl carbonyl compounds. The resulting cyclic polyaspartate is secondary polyamine and it can be used as reactive components for polyisocyanates in two-component cyclic polyurethane compositions and for preparing high quality coatings that are hard, elastic, heat resistant, abrasion resistant, solvent resistant and weather resistant.

The present invention relates to a novel polyesterimide, which is prepared by polycondensation of nadic imide based norbornane carboxylic acid and polyol or a hydroxyalkyl nadimide based norbornane carboxylic acid self polycondensation as illustrated in the following reaction.

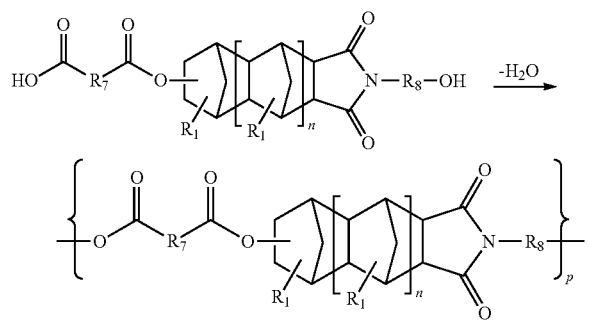

When nadimide based unsaturated carboxylic acid undergoes polycondensation with diols unsaturated polyesterimides are then formed. The unsaturated polyesterimides are curable with free radical initiators such as benzoyl peroxide to yield crosslinked polyesterimides, which may be used for the production of fiber reinforced resins. The unsaturated polyesterimide resins are illustrated in U.S. Pat. No. 5,427,881, which discloses a curable polyesterimide resin for high gloss toner applications.

The cyclic aliphatic polyamides are formed by reacting dicarboxylic acid with a norbornane structure component with diamine or polyamine. The amide link is produced from the condensation reaction of an amine group and a carboxylic acid group and water is eliminated as illustrated in the following reaction.

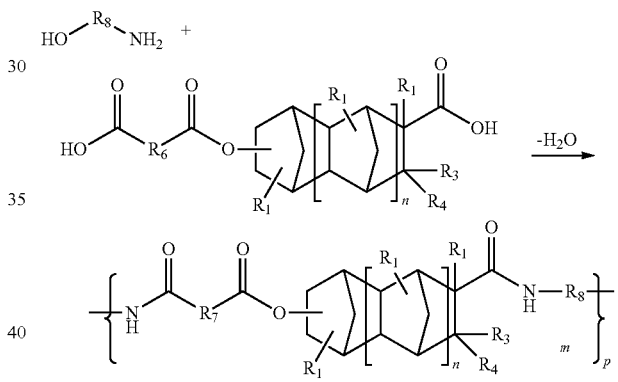

Examples of useful diamines include ethylenediamine, 1,2-propylenediamine, 1,3-propylenediamine, tetramethylenediamine, pentamethylenediamine, hexamethylenediamine, octamethylenediamine, 2-methyl-1,5-pentanediamine, and mixtures thereof.

These aliphatic cyclic polyamides may be prepared using conventional procedures and reaction conditions known to the art. In general, the norborane acid and amine component may be reacted at temperatures from about 100° C. to about 300° C. for from about 2 to about 24 hours until the final product has an acid value and an amine value less than 30 or until the theoretical amount of water is evolved. The reaction is preferably conducted under a nitrogen atmosphere and during the final stages of the reaction a vacuum is applied to the system to facilitate removal of the final traces of water and any other volatile materials. The monocarboxylic acids may be added to control the melt viscosity of the resulting polyamide.

When excess amount of multifunctional amine compound, such as ethylenediamine is used, it is possible to prepare an amine group end capped polyesteramide, which may be useful as cure agent for epoxy resin.

In preparing the polyester in accordance with the process of this invention, the molecular weight, viscosity, acid or hydroxyl number, glass transition temperature and softening point of the resulting polymer can be adjusted by a suitable choice of the combination of the diene/dienophile, acid/glycol structure, ratio, reaction temperature and reaction time.

The cyclic polyester prepared by above methods of this invention may be used as a solid such as powder for powder coating or may be dissolved in solvent or monomer. For coating application the polyester may be dissolved in solvent such as petroleum distillate, ester, glycol ether, alcohol, ketone and white spirit as solvent-borne coating. Examples include benzene, toluene, xylene, ethanol, isopropanol, acetone, ethyl methyl ketone, isobutyl methyl ketone, cyclohexanone, ethyl acetate and butyl acetate. Water may be used as diluent for water-borne cyclic polyester paints.

The reactive cyclic polyester prepared in this invention may be diluted with reactive solvent or monomer to form a curable composition under the action of heat, initiator or UV radiation.

The reactive solvent or monomer used in the present invention is preferably an unsaturated compound having one or more polymerizable double bonds in one molecule. Examples of reactive solvent include styrene, (meth)acrylic acid and esters thereof, such as methyl (meth)acrylate, ethyl (meth)acrylate, 2-hydroxyethyl (meth)acrylate, (meth) acrylic acid, ethylene glycol di(meth)acrylate, trimethylolpropane tri(meth)acrylate, oligoester (meth)acrylate, urethane (meth)acrylate oligomer, (meth)acrylic-modified epoxy oligomer, epoxy-modified acrylic urethane oligomer, (meth)acrylate oligomer, dialkyl fumarate, monoalkyl fumarate, dialkyl maleate, monoalkyl maleate. These compounds may be used alone or in combination.

The amount of the reactive solvent or monomer used in the present invention is usually 60% by weight or less.

The resulting polyester may be blended with other resin or formulated with different pigment and filler, such as titanium dioxide, talcs, clays or different additives, such as catalyst, stabilizer, and thickener. When reinforced with carbon fiber or fiberglass the curable polyester may be used to manufacture reinforced thermoset plastic.

According to the present invention, the production described above for functional norbornane derivative or polymer may be adapted by carrying out the two or three reaction steps in a one-pot process, which is desirable to address economic and environmental concerns.

The Diels-Alder reaction and acid addition reaction of Diels-Alder adduct with carboxylic acid may be done in two steps with separated reactors. The process is also preferably carried out as a one-pot process, i.e. the Diels-Alder reaction and acid addition of resulting Diels-alder adduct are carried out in one and the same reaction vessel without isolation of the intermediates. If the final product is a cyclic polyester it is prefer to carry out Diels-Alder reaction, acid addition of Diels-alder adduct and polycondensation of acidic norbornane all of three reactions in the same reactor without isolation of the intermediates.

In this one-pot process maleic acid can be prepared in situ, or one-pot, from hydrolysis of maleic anhydride and cyclopentadiene can be prepared in situ from cracking of dicyclopentadiene. Some reactants may work as both reactant and solvent or reactant and catalyst. For example dicyclopentadiene may work as solvent and diene for Diels-Alder reaction, maleic acid may work as dienophile for Diels-Alder reaction and as carboxylic acid for addition the resulting norbornene derivative, glycerine may first work as solvent for Diels-Alder reaction and follow by reacting with carboxyl compound to form a polyester.

In this one pot-process the different reactions may simultaneously happen. For example when acrylic acid or maleic half ester is heated with dicyclopentadiene at about 140-220° C. in addition to the Diels-Alder reactions of dienophile double bond with the cyclopentadiene from decomposition of dicyclopentadiene, carboxyl acids also undergo typical acid insert double bond reaction of resulting norbornene rings, i.e. acid addition. As the result of Diels-Alder and self-hydrocarboxylation the molecular weight of the product increased and acid number of product decreased. It is a feature of the present invention to provide economical one-pot self-catalytic process for the preparation of cyclic polyester.

Industry Application

The functional norbornane derivatives provided by this invention have great economic significance as important versatile intermediates for the chemical industry.

The oligomeric norbornenyl derivatives prepared by SASC process can be useful raw materials for not only for hydrocarboxylation but also for hydrogenation, hydroesterification, hydroxylation, oxidization, epoxidation, metathesis polymerization and free radical polymerization.

As multi-functional cycloaliphatic acid components they may be used as a chemical raw material in production of polyester, polyesterimide, polyamide for plastic, fiber, coating, ink, adhesive etc.

The new norbornanyl dicarboxylic acids can be used to prepare functional polymer such as reactive polyester. The reactive polyester can be prepared by esterification reaction or the ester-exchange reaction of a norbornanedicarboxylic acid derivative thereof with an alcohol component of a polyhydric alcohol. Depending on the ratio of acid to hydroxyl the obtained polyester will have a hydroxyl group and/or a carboxyl group at the terminals, and these terminal groups are reactive groups that may react with a curing agent to form a cured product.

For example, when the reactive polyester resin has a carboxyl group at the terminal, curing agent is preferably an epoxy compound having an epoxy such as epoxy resin or acrylic resin containing a glycidyl group. When the reactive polyester resin has a hydroxyl group at the terminal the curing agent may be an isocyanate compound such as aliphatic polyisocyanate and a blocked isocyanate compound or an amino compound.

Hydroxyl-terminated polyesters are the most common polyols, which are crosslinked through isocyanate groups. Generally, polyester polyols can achieve high solid coatings with great solvent resistance and good adhesion to metals. Polyester resins for coating applications are usually prepared with both aromatic and aliphatic dibasic acids. Isophthalic acid is the principal aromatic dibasic acid used in coatings, and adipic acid is the principal aliphatic diacid. The aromatic diacid compound is used to increase the glass transition temperature (Tg), hardness, and chemical resistance. However, the phenyl ring readily absorbs UV light which limit the photo-oxidative stability of the polyester and the polyester from aromatic acid usually has higher viscosity. The advantage of non-aromatic norbornanyl cyclic acid is that it not only has better weather resistance but also enables the preparation of low VOC (volatile organic compounds) resin with lower viscosity.

According to this invention it is possible to design and synthesize functional polymers with different reactive group, crosslinking density, Tg, soften point, molecular weight by select different dienes, dienophiles and carboxyl compounds. It is possible to adjust Tg of polymers by adjusting the weight ratio of bridged rings in molecules.

According to this invention these new norbornanedicarboxylic acids can be used to prepare novel polyesters for plastic materials. The cyclic polyesters have a high heat resistance, a low water absorption property, a low optical anisotropy, and a good moldability; it may be useful as an optical materials, electronic information materials, and medical device materials.

The norbornane compositions with carboxylic acid group have similar physical properties as natural rosin, which is a mixture of monocarboxylic diterpene acids with a softening point from about 70° C. to about 85° C. and an acid number from about 150 to 190 mg KOH/g. With adjustable soften point and acidity, better color and constant structure the acidic norbornane derivatives provided in this patent may be used as an synthetic substitute to natural rosin for the manufacture of adhesives, paper sizing agents, printing inks, solders and fluxes, various surface coatings, insulating materials for the electronics industry, synthetic rubber, chewing gums, soaps, and detergents.

If a dicarboxylic acid with norbornane structure compositions is reacted with long-chain aliphatic monohydric alcohol a low viscosity polyester is produced, which can be used as a non-aromatic plasticizers, a compatibilizer, a surface-tension modifier and a pigment dispersing agent. It is also possible to produce pour point depressant for diesel oil, lubricating oil, automatic transmission oil, hydraulic oil, home heating oil, and crude oil. The presence of pour point depressant will allow these oils to flow freely at lower temperatures. The pour point depressant can be prepared by esterification of norbornane acid with alcohol containing long alkyl group.

The cyclic polyester of the present invention may also be useful as a viscosity index improver and a thickening agent for mineral lubricating oil and a synthetic lubricating oil to improve the application properties such as oxidation stability, viscosity index, shear stability and low-temperature viscosity. To be used as an additive for lubricating oil the cyclic polyester should have a weight average molecular weight (Mw) of 20,000 to 400,000 for the good viscosity index improvement, the shear stability, and solubility. To prevent corrosion and poor solubility, the polyester should have an acid value less than 5 mg KOH/g and a hydroxyl value less than 20 mg KOH/g.

It is possible to use this norborane carboxylic acid to prepare a polycarbonate diol, which is suitable for polyurethane based adhesives and coating. Polycarbonate diol is prepared from the transesterification reaction of cyclic polyester diol with carbonate such as dimethyl carbonate.

Acrylic esters or methacrylic esters of cyclic polyester diol or polyol can be prepared by the esterification reaction of acrylic acid or methacrylic acid. Acrylic polyester containing a polycyclic hydrocarbon skeleton in the molecule is curable compositions and suitable as weathering-stable coating or adhesives that cure at high rates when exposed to radiation or free radicals.

The norborane carboxylic acid and its ester derivative can be useful as hydrocarbon resin or petroleum resin, which are commonly made by polymerization of unsaturated aliphatic petroleum hydrocarbon feedstocks. Compared with traditional hydrocarbon resins the norborane carboxylic acid and its polyester have improved colour and weathering-stability. It is easily to achieve desirable balance of the acid number, melt viscosity, softening point, alkyd compatibility, pigment dispersibility etc by properly adjusting the reaction conditions and the structures of diene, dienophile and carboxylic acid. With the properties similar to hydrocarbon resin or petroleum resin the novel norbornanyl resin can be useful as tackifier or binder for a lot of applications, such as hot-melt adhesive, pressure sensitive adhesives, sealant, traffic paint, or printing ink.

One of the possible applications for this novel norbornane acid and polyester is preparation of amorphous polyester resin. The esterification of norbornane acid and terephthalate with ethylene glycol or just blending amorphous norbornane polester with crystalline polyethylene terephthalate (PET) may disrupt the crystalline structure and produce an amorphous polyester composition. The amorphous polyesters are widely used for packaging materials or extruded objects due to their higher optical clarity, impact resistance, and ease process.

The lactone-containing compound has both polarity and rigidity and can be useful for the production of new polymeric materials such as a resin to formulate a coating with high rigidity and weather resistance or to form a film with both high transparency to the exposure light and rigidity. The structurally hindered nature of the bridged ring makes it more hydrolysis resistant than a linear ester structure.

The present invention relates to a polyesterimide containing bulky bridged cyclic hydrocarbon skeleton, which offers high glass transition temperature, low coefficient of linear thermal expansion. Polyimide is a known polymer with outstanding heat stability and mechanical property but it is hard to process and not available for application in solution processing because it is insoluble in general organic solvents or monomers. The incorporation of ester section makes the polyesterimide soluble in reactive solvents. The novel polyesterimide with good heat stability, filming ability and solubility produced in this invention is easy to process and can be useful in producing insulating coating of magnet wire, toner composition etc.

Usually the aliphatic polyamides are made with linear dicarboxylic acid such as adipic acid for nylon-66. One disadvantage of these linear aliphatic polyamides is that they may undergo dimensional and stiffness change due to moisture absorption. Aliphatic polyamides provided in this invention contain bulky cyclic norbornane structure and are less susceptible to moisture absorption and may lead to a new type of nylon with better stability of dimension and stiffness.

The synthetic strategy of this invention involving Diels-Alder reaction and modification of Diels-Alder adduct, subsequent acid addition not only provides great application opportunities in organic synthesis but also opens a door for green chemistry. For example biobased acrylic acid, fumaric acid, maleic acid, furan, itaconic acid can be used for Diels-Alder adduct. The biobased carboxylic acid such as succinic acid, malic acid, glutaric acid, malonic acid, citric acid, tartaric acid, aspartic acid, 3-hydroxy propionic acid can be used for acid addition of norbornenyl double bond. Thus, plastics or coating can now be made from renewable sources, which reduces consumption of petroleum based starting materials.

EXAMPLE

The following Examples are being supplied to further define various species of the present invention, it being noted that these examples are intended to illustrate and not limit the scope of the present invention. Parts and percentages are by weight unless otherwise indicated.

Viscosity was measured by Brookfield Viscometer. Softening point was measured by LP-16 Softening Point Ring and Ball Apparatus.

The molecular weight is measured by the gel permeation chromatography (GPC) and the glass transition temperature (Tg) is measured by the differential scanning calorimetry (DSC).

Gel time test involves determining the gel time, cure time and peak temperature for a formulation catalyzed with 1% benzoyl peroxide maintained at 180° F. (82.2° C.) in a water bath. The gel time is defined as the time required to go from 150° to 190° F. The cure time is defined as the time from 190° F. to the peak temperature (the total time to peak is the sum of the two), and peak temperature (or peak exotherm) is the maximum temperature attained by the sample during cure. These parameters are a representation of the lead time, reactivity and rate of cure for any curable formulation.

The Abbreviations used in the example are as follows.
DCPD: Dicyclopentadiene
Nadic acid: 5-Norbornene-2,3-dicarboxylic acid
Nadic anhydride: 5-Norbornene-2,3-dicarboxylic anhydride
$NBCO_2H$: 5-Norbornene-2-carboxylic acid
$MNBCO_2H$: 2-Methyl-5-norbornene-2-carboxylic acid
$MAc-NBCO_2H$: Adduct of maleic acid and $NBCO_2H$
$MAc-MNBCO_2H$: Adduct of maleic acid and $MNBCO_2H$
$NLCO_2H$: 2,6-Norbornane carbolactone-3-carboxylic acid
NPG: Neopentyl glycol
PG: Propylene glycol
EG: Ethylene glycol
DEG: Diethylene glycol
TMP: Trimethylolpropane
THQ: Toluhydroquinone
pTSA: p-Toluenesulfonic acid

SPECIFIC EMBODIMENTS

Example 1

Preparation of 5-Norbornene-2-Carboxylic Acid ($NBCO_2H$)

To a three-neck, round-bottom flask equipped with a mechanical stirrer, a Dean-Stark trap, a nitrogen inlet, and a water condenser were charged freshly distilled cyclopentadiene (198.3 g, 3.0 moles) to a solution of freshly distilled acrylic acid (216.2 g, 3.0 moles). The solution had a temperature between 5° C. and 10° C. The exothermic reaction was controlled by an ice bath. The cyclopentadiene was added to the solution over a period of one hour and after all the cyclopentadiene had been added, the solution was allowed to warm to ambient temperature. After a reaction period of 16 hours, gas chromatographic (GC) analysis indicated a $NBCO_2H$ mixture of isomers with 83% purity and about 2% adduct of cyclopentadiene and acrylic acid dimer.

Example 2

Preparation of $MAc-NBCO_2H$ Dicarboxylic Acid

Maleic acid (160.0 g, 1.38 mole) was added at in 60° C. to the $NBCO_2H$ (276.4 g, 2.00 mole) prepared in Example 1. The exothermic reaction was kept one hour at 60-90° C. and one hour at in 90-110° C. Maleic acid (84.0 g, 0.72 mole) was added and reacted for about 2 hours at 110-120° C. and one hour at 120-130° C. to obtain a $MAc-NBCO_2H$ dicarboxylic acid with an acid number of 413 mg KOH/g.

Example 3

Preparation of $MAc-NBCO_2H$ Dicarboxylic Acid

Water (7.2 g, 0.40 mole) was added in 4 times with stirring to a solution of maleic anhydride (33.4 g, 0.34 mole) and the $NBCO_2H$ (46.0 g, 0.33 mole) prepared in Example 1 at 90-100° C. After all water was added the reaction was kept between 100-120° C. for about 4 hours to obtain a $MAc-NBCO_2H$ dicarboxylic acid with an acid number of 416 mg KOH/g.

Example 4

Preparation of $MAc-NBCO_2H$-EHA Diester $MAc-NBCO_2H$ (51.0 g, 0.20 mole) prepared in Example 2,2-ethyl-1-hexanol (EHA) (78.0 g, 0.60 mole), pTSA (1.0 g) and toluene (40 g) were allowed to react at 100-120° C. under nitrogen until an acid number of 3 mg KOH/g was obtained. The resulting solution was allowed to cool to 30° C. and washed with water. After vacuum distillation to remove extra 2-ethyl-1-hexanol and toluene, 101 g of ester liquid product was obtained.

Example 5

Preparation of $MAc-NBCO_2H$-NPG Polyester $MAc-NBCO_2H$ (127.1 g, 0.50 mole) prepared in Example 2 and neopentyl glycol (NPG) (62.5 g, 0.60 mole). The mixture was slowly heated to 190° C. in 6 hours under nitrogen and reacted at 190-200° C. until an acid number of 29 mg KOH/g was obtained. The resulting resin was allowed to cool to 120° C. to obtain a polyester with a molecular weight of Mw/Mn=4240/2230 by GPC. THQ (0.03 g) and styrene was added to yield a resin solution with 30% styrene. The resin solution has viscosity 520 cps, a gel time 8.0 min, cure time 11.0 min, and peak exotherm 183° C.

Example 6

Preparation of $NBCO_2H$-NPG-MAn Polyester

To a three-neck, round-bottom flask equipped with a mechanical stirrer, a Dean-Stark trap, a nitrogen inlet, and a water condenser were charged $NBCO_2H$ (55.3 g, 0.40 mole) prepared in Example 1 and NPG (56.2 g, 0.54 mole). The mixture was allowed to react at 190-200° C. until an acid number of 57 mg KOH/g was obtained. Maleic anhydride (39.2 g, 0.40 mole) was added and the reaction was kept for 7 hours at 190-200° C. until an acid number of 28 mg KOH/g was obtained. The molecular weight of resulting polyester is Mw/Mn=2040/1490.

Example 7

Preparation of $NBCO_2H$-FA-NPG Polyester $NBCO_2H$ (69.1 g, 0.50 mole) and fumaric acid (58.0 g, 0.50 mole) were slowly heated to 190° C. and reacted at 190-200° C. for 4 hours under nitrogen. NPG (67.7 g, 0.65 mole) was added and the reaction was kept for another 6 hours at 195-200° C. until an acid number of 25 mg KOH/g was obtained. The molecular weight of the resulting polyester is Mw/Mn=4810/2350.

Example 8

Preparation of $MAc-NBCO_2H$-NPG Polyester by a One-Pot Process

To a three-neck, round-bottom flask equipped with a mechanical stirrer, a parked column with Dean-Stark trap, a dropping funnel, a nitrogen inlet, and a water condenser was charged NPG (94.0 g, 0.90 mole) and heated to 195-200° C., a solution of acrylic acid (47.0 g, 0.65 mole), DCPD (purity: 95%) (47.0 g, 0.36 mole) and THQ (0.08 g) were added slowly in 4 hours at 195-200° C. and kept at 195-200° C. for 2 hours until an acid number of 26 mg KOH/g was obtained. A 40% maleic acid water solution (188.0 g, 0.65 mole) was added and reaction was kept at 75-100° C. for 3 hours, 100-125° C. for 3 hours and 200° C. for 6 hours until an acid number of 25 mg KOH/g was obtained. The molecular weight of the resulting polyester is Mw/Mn=2220/1610.

Example 9

Preparation of MAc-NBCO$_2$H-NPG-DCPD Polyester

Water (11 g, 0.61 mole) was added in 4 times with stifling to a solution of maleic anhydride (49.0 g, 0.50 mole) and the NBCO$_2$H (69.1 g, 0.50 mole) at 90-100° C. After all water was added the reaction was kept at 100-120° C. for about 6 hours until an acid number of 408 mg KOH/g was obtained, and NPG (58.3 g, 0.56 mole) was added. The reaction was kept for another 9 hours at 200° C. until an acid number of 22 mg KOH/g was obtained. DCPD (33.0 g, 0.25 mole) was added from a dropping funnel in 30 min in 200° C. and kept reaction at 200° C. for 2 hours. The resulting polyester was allowed to cool to 120° C. and toluene was added to yield a clear resin solution with toluene.

Example 10

Preparation of 2-Methyl-5-Norbornene-2-Carboxylic Acid (MNBCO$_2$H), MAc-MNBCO$_2$H Dicarboxylic Acid and Acrylic Ester of MAc-MNBCO$_2$H Dicarboxylic Acid Dicyclopentadiene (111.0 g, 0.84 mole), methacrylic acid (86.1 g, 1.00 mole) and THQ (0.2 g) were stirred at 150° C. for 10 hours and the resulting crystal was filtered to obtain MNBCO$_2$H (120.0 g, 79% yield). MNBCO$_2$H (103.0 g, 0.68 mole) and water (14.1 g, 0.78 mole) were heated to 80° C. and maleic anhydride (67.6 g, 0.69 mole) was added in 4 times with stifling at 80-90° C. The reaction was kept between 110° C. and 120° C. for about 9 hours to obtain a dicarboxylic acid (MAc-MNBCO$_2$H) with an acid number of 388 mg KOH/g.

The resulting MAc-MNBCO$_2$H (115.7 g, 0.43 mole), benzyltriethylammonium chloride (0.11 g) and THQ (0.08 g) were heated to 80° C., glycidyl methacrylate (128.0 g, 0.90 mole) was added in 4 times under air. The mixture was allowed to react at 110-120° C. for 14 hours until an acid number of 13 mg KOH/g was obtained. The resulting resin was blended with styrene to yield a resin solution with 20% styrene. The viscosity of the resin solution is 630 cps.

Example 11

Preparation of NBCO$_2$C$_2$H$_5$, MAc-NBCO$_2$C$_2$H$_5$ Carboxylic Acid and Polyester Freshly distilled cyclopentadiene (80.0 g, 1.21 mole) was slowly dropped to ethyl acrylate (120 g, 1.20 mole) in 2 hours. The solution was kept at temperature between 20° C. and 40° C. After all the cyclopentadiene had been added, the solution was kept at temperature 25-40° C. for a reaction period of 14 hours. Maleic anhydride (49.0 g, 0.50 mole) was added in 4 times with stirring to the mixture of resulting NBCO$_2$C$_2$H$_5$ (83.1 g, 0.50 mole) and water (10.0 g, 0.56 mole). The reaction was kept between 100° C. and 125° C. for about 12 hours to obtain MAc-NBCO$_2$C$_2$H$_5$ with an acid number of 224 mg KOH/g. The obtained MAc-NBCO$_2$C$_2$H$_5$ (214.0 g) and NPG (99.3 g, 0.95 mole) were allowed to react at 190-200° C. until an acid number of 25 mg KOH/g was obtained. The resulting resin was blended with styrene to yield a resin solution with 25% styrene. The viscosity of the resin is 490 cps.

Example 12

Preparation of MAc-NBCO$_2$H-PAn-Fatty Acid-Glycerine Polyester

To a three-neck, round-bottom flask equipped with a mechanical stirrer, a Dean-Stark trap, a nitrogen inlet, and a water condenser were charged MAc-NBCO$_2$H (50.8 g, 0.20 mole), soyabean fatty acid (53.0 g, 0.26 mole), phthalic anhydride (50.0 g, 0.34 mole), glycerine (50.0 g, 0.54 mole) and xylene (22.0 g). The mixture was allowed to react at 190-200° C. until an acid number of 11 mg KOH/g was obtained. The resulting resin was allowed to cool to 120° C. and added xylene to yield a clear resin solution with 45% xylene.

Example 13

Preparation of Malic Acid-NBCO$_2$H-Man-PG Polyester

D.L-Malic acid (27.0 g, 0.20 mole) and NBCO$_2$H (60.8 g, 0.44 mole) were heated to 110-125° C. under nitrogen and held for 6 hours to an acid number of 423 mg KOH/g. Maleic anhydride (39.2 g, 0.40 mole) and PG (61.0 g, 0.80 mole) were added into the solution and heated to 200-210° C. and stirred at 200-210° C. for 15 hours until an acid number of 7 mg KOH/g was obtained. After cool to 120° C. the resulting polyester having a molecular weight of Mw/Mn=11160/2280 was dissolved in styrene with 0.03 g of THQ to obtain a resin with 30% styrene. The resin has a viscosity of 700 cps, gel time 7.0 min, cure time 8.4 min, and peak exotherm 229° C.

Example 14

Preparation of MAc-NBCO$_2$H-CPD Oligomeric Dicarboxylic Acid

Maleic acid (46.5 g, 0.40 mole) and NBCO$_2$H (60.8 g, 0.44 mole) were heated to 110-130° C. under nitrogen and held for 5 hours to an acid number of 364 mg KOH/g. The temperature was increased to 190° C. in 3 hours, and dicyclopentadiene (53.0 g, 0.40 mole) was dropped into the solution in one hour at 190-196° C. and stirred at 200-210° C. for 15 hours to obtain an oligomeric dicarboxylic acid with an acid number of 139 mg KOH/g. The resulting oligomeric acid is a rosin-like solid in room temperature.

Example 15

Preparation of Norbornene Carbonitrile (NBCN)

Freshly distilled cyclopentadiene (112.0 g, 1.69 mole) was slowly dropped to acrylonitrile (90.0 g, 1.69 mole) in 2 hours. The solution was kept at temperature between 13° C. and 45° C., after all the cyclopentadiene had been added, the solution was kept at temperature 25-40° C. for a reaction period of 14 hours, gas chromatographic (GC) analysis indicated endo/exo norbornene carbonitrile with isomer ratio of endo/exo=1.8/1.0.

Maleic acid (116.0 g, 1.18 mole) was added in 4 times with stirring to the resulting NBCN (119.0 g, 1.00 mole). The reaction was kept between 100° C. and 125° C. for about 6 hours. The acid number of the product was 310 mg KOH/g, NPG (57.6 g, 0.55 mole) was added and heated to 200-210° C. and held for 6 hours to an acid number of 43 mg KOH/g to obtain a polyester. The resulting polyester was dissolved in styrene with 0.03 g of THQ to obtain a resin with 35% of styrene, the resin solution has viscosity of 3300 cps.

Example 16

Preparation of Adipic Acid-NBCO$_2$H Oligomeric Dicarboxylic Acid

NBCO$_2$H (165.8 g, 1.20 mole) and adipic acid (43.8 g, 0.30 mole) were heated to 205° C. under nitrogen and held for 16 hours to obtain a dicarboxylic acid with an acid number of 207 mg KOH/g, the obtained dicarboxylic acid is a light yellow rosin-like solid in room temperature with a molecular weight of Mw/Mn=960/630.

Example 17

Preparation of NBCO$_2$H Oligomeric Acid and Polyester

NBCO$_2$H (39.0 g, 0.28 mole) was heated to 200-225° C. and held for 15 hours under nitrogen to obtain a cyclic oligomeric carboxylic acid with an acid number of 93 mg KOH/g, a softening point of 142° C., a Tg of 72° C. and a melting viscosity of 82 p at 200° C. The obtained oligomer (33.0 g) and glycerine (18.5 g, 0.20 mole) were heated to 200-220° C. and held for 4 hours to an acid number of 4 mg KOH/g, adipic acid (10.5 g, 0.07 mole) was added, heated to 220° C. and held for 3 hours to obtain a polyester with an acid number of 8 mg KOH/g and molecular weight of Mw/Mn=6740/1720.

The same NBCO$_2$H (39.0 g, 0.28 mole) was heated to 200-225° C. and held for 15 hours, then heated to 230-240° C. and held for 7 hours under nitrogen to obtain an oligomeric carboxylic acid with an acid number of 85 mg KOH/g, a softening point of 150° C., a Tg of 90° C. and a melt viscosity of 139 p at 200° C.

Example 18

Preparation of Adipic Acid-NBCO$_2$H-NPG Polyester

NBCO$_2$H (160.0 g, 1.16 mole) was heated to 200-220° C. and held 11 hours to an acid number of 107 mg KOH/g, adipic acid (45.0 g, 0.31 mole) was added and heated to 200-220° C. and held for 8 hours to obtain a oligomeric dicarboxylic acid with an acid number of 247 mg KOH/g, NPG (57.8 g, 0.55 mole) was added and heated to 200-210° C. and held for 8 hours to obtain a polyester with an acid number of 19 mg KOH/g. The resulting polyester (having a molecular weight of Mw/Mn=2060/1190) was dissolved in toluene to obtain a clear resin with 40% toluene, the resin solution has a viscosity of 150 cps.

Example 19

Preparation of Adipic Acid-NBCO$_2$H-NPG Polyester

NBCO$_2$H (69.1 g, 0.50 mole) and adipic acid (73.1 g, 0.50 mole) were heated to 200-215° C. under nitrogen and held for 8 hours to obtain a dicarboxylic acid with an acid number of 398 mg KOH/g, NPG (62.5 g, 0.60 mole) was added and heated to 200-210° C. and held for 4 hours to obtain a polyester with an acid number of 25 mg KOH/g and a molecular weight of Mw/Mn=2820/1360.

Example 20

Preparation of Adipic Acid-NBCO$_2$H-NPG Polyester

NBCO$_2$H (94.0 g, 0.68 mole) and adipic acid (49.8 g, 0.34 mole) were heated to 200-220° C. under nitrogen and held for 9 hours to obtain a dicarboxylic acid with an acid number of 287 mg KOH/g, NPG (49.0 g, 0.47 mole) was added and heated to 200-210° C. and held for 6 hours to obtain a polyester with an acid number of 21 mg KOH/g and a molecular weight of Mw/Mn=2410/1320.

Example 21

Preparation of Adipic Acid-NBCO$_2$H Polyamide, Diester and Acrylic Ester

NBCO$_2$H (138.2 g, 1.00 mole) and adipic acid (146.1 g, 1.00 mole) were heated to 200° C. under nitrogen and held for 11 hours to obtain a dicarboxylic acid (E21-A) with an acid number of 405 mg KOH/g, the obtained dicarboxylic acid (85.3 g, 0.30 mole) and 2-ethyl-1-hexanol (78.1 g, 0.60 mole) were heated to 185° C. and held for 17 hours to obtain a diester with an acid number of 25 mg KOH/g.

The same dicarboxylic acid (E21-A) obtained from above example (85.3 g, 0.30 mole) and ethylenediamine (18.0 g, 0.30 mole) were heated to 200-220° C. under nitrogen and held for 8 hours to get 11.0 g of water (close to theoretical amount) out. The obtained polyamide is insoluble in methanol for acid number test and also insoluble in THF for GPC test.

The same dicarboxylic acid (E21-A) obtained from above example (85.3 g, 0.30 mole), glycidyl methacrylate (86.7 g, 0.61 mole), THQ (0.09 g) and triethyl benzyl ammonium chloride (0.15 g) were heated to 110-117° C. and held for 6 hours to obtain a acrylic ester with an acid number of 11 mg KOH/g. The resulting acrylic ester was dissolved in styrene with 0.01 g of THQ to obtain a resin with 31.5% styrene. The resin solution has a viscosity of 65 cps, gel time 19.4 min, cure time 20.5 min, and peak exotherm 230° C.

Example 22

Preparation of TMPTA-CPD, FA-TMPTA-CPD Carboxylic Acid and Acrylic Ester

Trimethylolpropane triacrylate (177.8 g, 0.60 mole) and cyclopentadiene (112.0 g, 1.8 mole) were stirred at 25-40° C. for 21 hours to obtain Diels-Alder adduct of TMPTA-CPD. The obtained TMPTA-CPD (165.0 g, 0.33 mole), fumaric acid (38.3 g, 0.33 mole) and THQ (0.07 g) were heated to 190° C. in 3 hours under nitrogen and held for 12 hours to obtain a oligomeric acid with an acid number of 55 mg KOH/g, glycidyl methacrylate (28.4 g, 0.20 mole) and benzyltriethylammonium chloride (0.15 g) were heated to 110-120° C. and held for 2 hours to obtain an acrylic ester with an acid number of 22. The resulting acrylic ester was dissolved in styrene with 0.04 g of THQ to obtain a resin with 30% styrene. The resin solution has a viscosity of 430 cps, gel time 9.0 min, cure time 12.0 min, and peak exotherm 210° C.

Example 23

Preparation of NBCO$_2$H Oligomeric Acid and NBCO$_2$H-NPG Polyester by One-Pot Process Dicyclopentadiene (80.0 g, 0.60 mole) and THQ (0.16 g) were heated at 180-190° C. under nitrogen, the mixture of dicyclopentadiene (160.0 g, 1.21 mole) and acrylic acid (160.0 g, 2.22 mole) were added by dropping in one hour at 180-190° C. and stirred at 190-220° C. for 14 hours to obtain a cyclic oligomeric carboxylic acid with an acid number of 107 mg KOH/g and a melt viscosity 22 p at 220° C. The obtained oligomer (56.5 g) was heated with NPG (11.5 g, 0.11 mole) to 200-215° C. and held for 6 hours to obtain a polyester with an acid number of 16 mg KOH/g, a Tg of 41° C., a soften point 98° C.

Example 24

Preparation of Adipic Acid-NBCO$_2$H-Glycerine Polyester by One-Pot Process

Adipic acid (73.0 g, 0.50 mole) was heated at 200-210° C. under nitrogen, the mixture of dicyclopentadiene (33.3 g, 0.25 mole) and acrylic acid (36.0 g, 0.5 mole) were added by dropping in one hour at 200-210° C. and stirred at 210-220° C. for 15 hours to an acid number of 407 mg KOH/g. The obtained oligomeric dicarboxylic acid was heated with glycerine (46.1 g, 0.50 mole) to 200° C. and held for 7 hours to obtain a polyester with an acid number of 24 mg KOH/g.

Example 25

Preparation of Adipic Acid-NBCO$_2$H-MAn-NPG Polyester by One-Pot Process

Adipic acid (73.0 g, 0.50 mole) was heated at 200°-210° C. under nitrogen, the mixture of dicyclopentadiene (33.3 g, 0.25 mole) and acrylic acid (36.0 g, 0.5 mole) was added by dropping in one hour at 200-210° C. and stirred at 210-220° C. for 15 hours to acid number of 407 mg KOH/g. The obtained oligomeric dicarboxylic acid was heated with maleic anhydride (57.1 g, 0.58 mole) and NPG (101.0 g, 0.97 mole) to 195° C. and held for 7 hours to obtain a polyester with an acid number of 12 mg KOH/g. The resulting polyester (having a molecular weight of Mw/Mn=4110/1720) was dissolved in styrene with 0.04 g of THQ to obtain a resin with 30% styrene, the resin solution has a viscosity of 340 cps, gel time 10.0 min, cure time 14.0 min, and peak exotherm 193° C.

Example 26

Preparation of Methyl-NBCO$_2$H, MAc-Methyl-NBCO$_2$H Dicarboxylic Acid and Polyester Freshly distilled methcyclopentadiene (160.3 g, 2.00 mole) from methcyclopentadiene dimer was added dropwise to acrylic acid (144.1 g, 2.00 mole) in 2 hours and the solution was kept at temperature between 25° C. and 40° C., after all the methcyclopentadiene had been added, the solution was kept at temperature 25-45° C. for a reaction period of 16 hours, gas chromatographic (GC) analysis indicated that the product contains 74% of endo/exo methyl-5-norbornene-2-carboxylic acid and 16% adduct of acrylic acid dimer with methcyclopentadiene.

Maleic acid (116.1 g, 1.00 mole) was added with stirring to the resulting adduct of methcyclopentadiene and acrylic acid (153.0 g). The reaction was kept between 100° C. and 125° C. for about 3 hours to obtain an unsaturated dicarboxylic acid with an acid number of 359 mg KOH/g, NPG (109.4 g, 1.05 mole) was added and heated to 190-200° C. and held for 8 hours to an acid number of 24 mg KOH/g. The resulting polyester was dissolved in styrene with 0.09 g of THQ to obtain a resin with 30% styrene, the resin solution has a viscosity of 500 cps and a gel time 13.2 min, cure time 17.1 min, and peak exotherm 208° C.

Example 27

Preparation of MAc-DCPD-Nadic Anhydride and Anhydride Cured Epoxy Resin

Nadic anhydride (164.2 g, 1.00 mole) and DCPD (66.1 g, 0.50 mole) were heated to 200° C. under nitrogen and held for 4 hours to obtain a DCPD-nadic anhydride. Maleic acid (93.0 g, 0.8 mole) was added at 110° C. and hold at 110-130° C. for 2 hours to obtained a clear liquid anhydride. The obtained anhydride (100 g) was mixed with epoxy resin (100 g, EEW 190), benzyltriethylammonium chloride (1.5 g) at 80° C. and degas with vacuum, the liquid resin was poured into a glass mold and heated at 80° C. for 4 hours, at 120° C. for 4 hours and at 150° C. for 2 hours to obtained a clear anhydride cured epoxy panel with a Tg of 135° C. tested by DSC.

Example 28

Preparation of MAn-NPG-DCPD Polyacid

Maleic anhydride (51.0 g, 0.52 mole), NPG (27.1 g, 0.26 mole) and DCPD (68.8 g, 0.52 mole) were heated to 130° C. under nitrogen and held for 2 hours to an acid number of 198 mg KOH/g. The temperature was increased to 200° C. in 3 hours and the solution was stirred at 195-205° C. to obtain a multi-functional norbornenyl carboxylic acid with an acid number of 84 mg KOH/g and a melt viscosity of 33 p at 150° C. The resulting multi-functional acid (58.2 g) was heated with NPG (9.3 g, 0.09 mole) at 200-208° C. for 4 hours and the resin gelled.

Example 29

Preparation of MAn-EHA-DCPD-MAc-EG Polyester by One-Pot Process

Maleic anhydride (39.2 g, 0.40 mole), 2-ethyl-1-hexanol (52.0 g, 0.40 mole) and dicyclopentadiene (53.0 g, 0.40 mole) were heated to 190° C. in 4 hours under nitrogen and held at 190-200° C. for 3 hours to an acid number of 99 mg KOH/g. The obtained oligomeric norbornenyl carboxylic acid (69.0 g) was heated with maleic anhydride (41.0 g, 0.42 mole) and water (7.50 g, 0.42 mole) to 110-125° C. and held for 3 hours to an acid number of 346 mg KOH/g, EG (33.0 g, 0.53 mole) was added and heated to 190-200° C. After stirring at 190-200° C. for 6 hours a polyester was obtained with an acid number of 22 mg KOH/g and a molecular weight of Mw/Mn=2500/970.

Example 30

Preparation of MAc-DCPD-EG Polyester by One-Pot Process

Maleic anhydride (29.4 g, 0.30 mole), water (6.0 g, 0.33 mole) and DCPD (159.0 g, 1.20 mole) were heated to 120° C.

in 2 hours under nitrogen and held at 110-125° C. for 3 hours to acid number of 84 mg KOH/g. The solution was heated to 200° C. in 9 hours and stirred at 200-205° C. for 15 hours to an acid number of 50 mg KOH/g and a melt viscosity 3 p at 150° C., during this process the distillate oil phase was returned back to reactor and only water was released out. The obtained oligomeric norbornenyl carboxylic acid (56.0 g) was heated with maleic anhydride (27.5 g, 0.28 mole) and water (5.0 g, 0.28 mole) were heated to 120-125° C. and held for 3 hours to acid number of 235 mg KOH/g, EG (21.0 g, 0.34 mole) was added and heated to 190-200° C. and stirred at 190-200° C. for 4 hours until an acid number of 29 mg KOH/g was obtained. The resulting polyester has a molecular weight of Mw/Mn=5850/1380.

Example 31

Preparation of MAc-DCPD-DEG Polyester by One-Pot Process

Maleic anhydride (49.0 g, 0.50 mole), water (9.1 g, 0.51 mole) and DCPD (132.2 g, 1.0 mole) were heated to 120° C. in 2 hours under nitrogen and held at 110-125° C. for 3 hours to acid number of 140 mg KOH/g. The solution was heated to 200° C. in 3 hours and stirred at 200-205° C. for 7 hours to an acid number of 89 mg KOH/g. The obtained oligomeric norbornenyl carboxylic acid (53.0 g) was heated with maleic anhydride (33.0 g, 0.34 mole) and water (6.1 g, 0.34 mole) to 120-125° C. and held for 4 hours to an acid number of 351 mg KOH/g, DEG (42.0 g, 0.40 mole) was added and heated to 190-200° C. and stirred at 190-200° C. for 4 hours until an acid number of 33 mg KOH/g was obtained. The resulting polyester (having a molecular weight of Mw/Mn=2060/1560) was dissolved in styrene with 0.03 g of THQ to obtain a resin with 30% styrene and a viscosity of 940 cps.

Example 32

Preparation of MAn-DCPD-PG Polyester by One-Pot Process

Maleic anhydride (70.0 g, 0.71 mole) and PG (100.0 g, 1.32 mole) were heated to 200-210° C. in 2 hours under nitrogen and held for 4 hours. DCPD (47.6 g, 0.36 mole) was added dropwise into the solution in 210-215° C. in 2 hours and held for one hour to obtain a norbornenyl diester. Maleic anhydride (64.6 g, 0.66 mole) and PG (20.0 g, 0.26 mole) were added and heated to 200° C. and stirred at 200° C. until an acid number of 19 mg KOH/g was obtained. The resulting polyester was dissolved in styrene with 0.03 g of THQ to obtain a resin with 30% styrene and a viscosity of 2300 cps.

Example 33

Preparation of MAn-DCPD-NPG Polyester by One-Pot Process

Maleic anhydride (64.0 g, 0.65 mole) and DCPD (172.0 g, 1.30 mole) were heated to 90° C. and water (12.0 g, 0.67 mole) was added dropwise into the reactor in 2 hours under nitrogen and held at 110-125° C. for 2 hours to an acid number of 145 mg KOH/g. The temperature was increased to 200° C. in 6 hours and held at 200-210° C. for 16 hours until an acid number of 56 mg KOH/g was obtained. The resulting oligomeric norbornenyl carboxylic acid (56.0 g) was heated with NPG (4.1 g, 0.39 mole) to 210-225° C. and stirred at 190-200° C. for 9 hours to obtain a polyester with an acid number of 28 mg KOH/g.

Example 34

Preparation of MAc-DCPD Oligomeric Norbornenyl Carboxylic Acid and Polyester by DAR One-Pot Process Maleic anhydride (49.0 g, 0.50 mole), water (10.0 g, 0.56 mole) and DCPD (132.2 g, 1.0 mole) were heated to 110° C. in 2 hours under nitrogen and held at 110-125° for 3 hours to an acid number of 156 mg KOH/g. The solution was heated to 200° C. in 5 hours and stirred at 200-205° C. for 5 hours to an acid number of 98 mg KOH/g. The obtained oligomeric norbornenyl carboxylic acid (82.0 g) was heated with maleic anhydride (20.0 g, 0.20 mole) and water (4.3 g, 0.24 mole) to 115-125° C. and held for 4 hours to obtain a maleic half ester with an acid number of 231 mg KOH/g, DCPD (28.0 g, 0.21 mole) was added and heated to 200-210° C., the solution was stirred at 200-210° C. for 5 hours to obtain a oligomeric norbornenyl acid (E34-A) with an acid number of 132 mg KOH/g, a melt viscosity 11 p at 125° C. and a molecular of Mw/Mn=540/120. The resulting norbornenyl oligomer acid E34-A (73.0 g) was heated with maleic anhydride (44.0 g, 0.45 mole) and water (8.2 g, 0.46 mole) to 115-125° C. and held for 3 hours to an acid number of 377 mg KOH/g, EG (45.0 g, 0.72 mole) was added, heated to 200-210° C. and stirred at 200-210° C. until an acid number of 24 mg KOH/g was obtained. The resulting polyester (having a molecular weight of Mw/Mn=3470/870) was dissolved in styrene with 0.04 g of THQ to obtain a resin with 30% styrene, the resin solution has a viscosity of 1080 cps, gel time 11.0 min, cure time 12.4 min, and peak exotherm 201° C.

The same resulting oligomeric acid E34-A (21.0 g) from above experiment was heated with NPG (4.0 g, 0.04 mole) to 200-210° C. and stirred at 200-215° C. for 7 hours until an acid number of 31 mg KOH/g was obtained. The resulting polyester (having a molecular weight of Mw/Mn=8190/610 and a melt viscosity 13 p at 200° C.) was dissolved in toluene to obtain a clear resin with 58% toluene and a viscosity of 130 cps.

Example 35

Preparation of MAc-Nadic-DCPD Carboxylic Acid and Polyester

DCPD (92.5 g, 0.70 mole) and maleic anhydride (19.6 g, 0.20 mole) were allowed to react at 155-165° C. under nitrogen for 2 hours to obtain a nadic anhydride solution. After the mixture was cooled to 100° C., maleic anhydride (58.8 g, 0.60 mole) and water (14.4 g, 0.80 mole) were added. The mixture was allowed to react at 100-125° C. for 3 hours. DEG (57.0 g, 0.54 mole) was added and the mixture was allowed to react at 200° C. until an acid number of 34 mg KOHg was obtained. The resulting polyester was allowed to cool to 100° C. and styrene was added to yield a resin solution with 30% styrene, the resin solution has a viscosity of 870 cps.

Example 36

Preparation of MAc-Nadic-NPG Polyester by One-Pot Process

Maleic anhydride (49.0 g, 0.50 mole) and NPG (156.2 g, 1.50 mole) were heated at 190-200° C. under nitrogen to obtain an oligomeric maleate with an acid number of 5 mg KOH/g, DCPD (33.0 g, 0.25 mole) was added by dropping at 190-200° C. in half hour and stirred at 200° C. for one hour and cool to 90° C. to obtain a Diels-Alder adduct. Maleic anhydride (82.0 g, 0.84 mole) and water (17.0 g, 0.90 mole) were added, heated to 120° C. and held for 3 hours to an acid number of 137 mg KOH/g. The reaction was allowed to react at 195° C. for 8 hours to an acid number of 16 mg KOH/g. The resulting polyester was dissolved in styrene with 0.03 g of THQ to obtain a resin with 30% styrene, the resin solution has a viscosity of 1420 cps.

Example 37

Preparation of MAc-MNadic-NPG Polyester

Methyl-5-norbornene-2,3-dicarboxylic anhydride (42.8 g, 0.24 mole), maleic anhydride (70.6 g, 0.72 mole) and water (36.0 g, 2.00 mole) were heated at 100-115° C. under nitrogen for 5 hours. NPG (96.3 g, 0.92 mole) was added and stirred at 200° C. for 6 hours to an acid number of 24 mg KOH/g. The resulting polyester was dissolved in styrene with 0.09 g of THQ to obtain a resin with 32% styrene and a viscosity of 750 cps.

Example 38

Preparation of MAc-Itaconic Acid-Cyclopentadiene Oligomeric Carboxylic Acid

Itaconic acid (130.1 g, 1.00 mole), isopropanol (300.0 g) and water (300.0 g) were heated at 25-30° C. under nitrogen, cyclopentadiene (66.1 g, 1.00 mole) was added to the solution in 3 times and the mixture was allowed to react at 30-60° C. for 8 hours, ⅔ of solvent was distilled out, and the resulting crystal was filtered out and crystallized with water to obtain 2-(carboxymethyl)bicycle[2.2.1]hept-5-ene-2-carboxylic acid (106.0 g, yield: 54%) with an acid number of 575 mg KOH/g (theoretical acid value 572). The obtained acidic adduct (98.1 g, 0.50 mole), maleic anhydride (49.0 g, 0.50 mole) and water (72.0 g, 4.00 mole) were heated to 110-130° C. and held for 5 hours to obtain an oligomeric carboxylic acid with an acid number of 565 mg KOH/g. NPG (100.0 g, 0.95 mole) was added and heated at 200° C. for 9 hours to obtain a polyester with an acid number of 39 mg KOH/g. The resulting polyester was dissolved in styrene with 0.07 g of THQ to obtain a resin with 47% styrene, it has a viscosity of 14000 cps and a gel time 15.1 min, cure time 17.2 min and peak exotherm 236° C.

Example 39

Preparation of N-(2'-hydroxethyl)-bicyclo-[2,2,1]-hept-5-ene-2,3-dicarboximide (Nadic imide), MAc-Nadic imide carboxylic acid and polyesterimide Nadic anhydride (164.2 g, 1.00 mole) was dissolved in 220 ml of toluene. To the mixture was slowly added ethanolamine (61.1 g, 1.00 mole) at 30-70° C. and then stirred for 7 hours at 100-120° C. to remove water and part of toluene. After sitting overnight at room temperature, the resulting yellow crystal was filtered and dried to obtain 143.0 g of nadic imide. $^1$H NMR (DMSO) δ 1.50 (m, 1H), 1.78 (m, 1H), 3.08 (s, 1H), 3.35 (m, 2H), 3.46 (m, 2H), 3.59 (m, 2H), 3.68 (m, 2H), 6.16 (d, 2H).

The obtained nadic imide (89.0 g, 0.43 mole), water (22.0 g, 1.22 mole) and maleic anhydride (84.6 g, 0.86 mole) were reacted at 80-115° C. for 8 hours to an acid number of 213 mg KOH/g. NPG (49.2 g, 0.47 mole) and THQ (0.03 g) were added and heated to 200° C. in 3 hours. The reaction was kept at 200-210° C. until an acid number of 33 mg KOH/g was obtained. After cooling to 120° C. the obtained polyesterimide was blended with styrene to make a solution with 30% of styrene with a viscosity of 1180 cps, gel time 6.3 min, cure time 8.3 min, and peak exotherm 227° C.

Example 40

Preparation of MAc-Nadic Imide-EG Polyesterimide by One-Pot Process

Maleic anhydride (67.0 g, 0.68 mole) and DCPD (90.0 g, 0.68 mole) were heated to 70° C. under nitrogen, ethanolamine (21.0 g, 0.34 mole) was added by dropping in one hour at 80-110° C. and heated to 200° C. in 6 hours and stirred at 200-205° C. for 4 hours to an acid number of 63 mg KOH/g. The obtained oligomeric nadic imide (50.0 g) was heated with maleic anhydride (30.0 g, 0.31 mole) and water (5.5 g, 0.31 mole) to 115-125° C. and held for 3 hours to an acid number of 346 mg KOH/g, EG (28.0 g, 0.40 mole) was added, heated to 195-200° C. and stirred at 200° C. for 6 hours until an acid number of 15 mg KOH/g was obtained. The resulting polyesterimide (having a molecular weight of Mw/Mn=2230/600) was dissolved in styrene with 0.03 g of THQ to obtain a resin solution with 30% styrene, the resin has a viscosity of 850 cps, gel time 6.1 min, cure time 8.4 min, and peak exotherm 187° C.

Example 41

Preparation of MAc-Nadic Imide-PG Polyesterimide

Maleic anhydride (49.0 g, 0.50 mole) and DCPD (66.1 g, 0.50 mole) were heated at 170-200° C. for 7 hours under nitrogen, ethanolamine (30.5 g, 0.50 mole) was added dropwise over half hour at 130° C. and stirred at 170-190° C. to an acid number of 2 mg KOH/g. The obtained oligomeric nadic imide was heated with maleic anhydride (58.8 g, 0.60 mole) and water (11.9 g, 0.66 mole) to 115-125° C. and held for 9 hours to an acid number of 205 mg KOH/g, PG (29.4 g, 0.39 mole) was added, heated to 195-210° C. and stirred at 210° C. for 8 hours until an acid number of 27 mg KOH/g was obtained. The resulting polyesterimide was dissolved in styrene with 0.03 g of THQ to obtain a resin solution with 30% styrene, with a viscosity of 5300 cps, gel time 2.5 min, cure time 4.3 min, and peak exotherm 225° C.

Example 42

Preparation of MAc-Nadic Imide-DEG Polyesterimide by One-Pot Process

Maleic anhydride (20.0 g, 0.20 mole) and DCPD (120.0 g, 0.91 mole) were heated to 160-170° C. and kept at reflux under nitrogen for 3 hours. After cooled to 25° C. ethanolamine (12.2 g, 0.20 mole) was slowly added and heated at 25-45° C. for 2 hours. The temperature was increased to 120-135° C. and kept for 2 hours to remove formed water. At 80° C. water (27 g) and maleic anhydride (98.1 g, 1.00 mole) were added. The solution was stirred at 110-125° C. for 4 hours. DEG (74.0 g, 0.70 mole) was added and temperature was kept at 200-210° C. for 6 hours to obtain a polyesterimide with an acid number of 25 mg KOH/g.

Example 43

Preparation of 2,6-Norbornane Carbolactone-3-Carboxylic Acid (NBLCO$_2$H)

Nadic anhydride (92.0 g), pTSA (19.0 g) and water (272.0 g) were slowly heated to 100° C. in 2 hours and kept reflux at temperature 100-105° C. for 16 hours. After stored at room temperature overnight the crystal was filtered out and dried to produce 81.0 g of NBLCO$_2$H. $^1$H NMR (DMSO) δ 1.50 (d, 1H), 1.56 (d, 1H), 1.60 (m, 1H), 1.93 (dd, 1H), 2.41 (m, 1H), 2.63 (dd, 1H), 2.92 (dt, 1H), 3.21 (t, 1H), 4.76 (dd, 1H).

Example 44

Preparation of NBLCO$_2$H-NPG-TMP-MAn Polyester

The obtained NBLCO$_2$H (73.0 g, 0.40 mole) from E-43, NPG (85.4 g, 0.82 mole), and trimethylolpropane (18.0 g, 0.13 mole) were heated at 185° C. for 14 hours until an acid number of 4 mg KOH/g was obtained. Maleic anhydride (66.0 g, 0.67 mole) was added and the temperature was increased to and maintained at 200° C. for 8 hours to obtain a polyester with an acid number of 25 mg KOH/g.

Example 45

Preparation of NBLCO$_2$H with MAn and DCPD

Maleic anhydride (88.3 g, 0.90 mole) and water (150.0 g) was stirred at 20-30° C. under nitrogen, cyclopentadiene (30.0 g, 0.45 mole) was added dropwise over 1 hour and stirred at 25° C. for 6 hours, it was heated to 101° C. and held for 20 hours until 92% of nadic acid was converted to NBLCO$_2$H as detected by GC. The wet crystal was filtered out and recrystallized from water to obtain 40.3 g of NBLCO$_2$H with a yield of 49%.

Example 46

Preparation of NBLCO$_2$H-MAc-NPG Polyester by One-Pot Process

Maleic anhydride (59.0 g, 0.60 mole) and water (100.0 g) were heated at 20°-30° C. under nitrogen, cyclopentadiene (20.0 g, 0.30 mole) was added by dropping in 1 hour and stirred at 25° C. for 8 hours, heated to 101° C. and held for 22 hours until 92% of nadic acid was converted to NBLCO$_2$H as detected by GC. NPG (78.2 g, 0.75 mole) was added, heated to 200° C. and held for 8 hours to an acid number of 6 mg KOH/g, maleic anhydride (30.0 g, 0.30 mole) was added, heated to 200° C. and held for 9 hours to obtain a polyester with an acid number of 12 mg KOH/g. The resulting polyester (having a molecular weight of Mw/Mn=7940/3130) was dissolved in styrene with 0.03 g of THQ to obtain a resin solution with 30% styrene, the resin has a viscosity of 2700 cps, gel time 7.4 min, cure time 9.4 min, and peak exotherm 225° C.

Example 47

Preparation of NBLCO$_2$H with Nadic Anhydride and Oxalic Acid and Polyester Nadic anhydride (32.8 g, 0.20 mole), oxalic acid dihydrate (32.8 g, 0.26 mole) and water (98.0 g) were heated at 100-104° C. under nitrogen for 4 hours, until 98% of nadic acid was converted to NBLCO$_2$H as detected by GC, trimethylolpropane (38.8 g, 0.29 mole) and FASCAT 4100 catalyst (0.03 g) were added, heated to 200° C. and held for 8 hours to obtain a polyester with an acid number of 18 mg KOH/g.

Example 48

Preparation of NBCO$_2$H-NPG-TMP Polyetherester Polyol

NBCO$_2$H (83.0 g, 0.60 mole), NPG (62.5 g, 0.60 mole) and trimethylolpropane (40.2 g, 0.30 mole) were heated to 220-240° C. under nitrogen and held for 10 hours to obtain a polyetherester polyol with an acid number of 0 mg KOH/g.

Example 49

Preparation of NBCO$_2$H-NPG-TMP Polyetherester Polyol

Glycerine (138.1 g, 1.50 mole) and THQ (0.16 g) were heated at 210° C. under nitrogen, the mixture of DCPD (66.1 g, 0.50 mole) and acrylic acid (72.1 g, 1.0 mole) were added by dropping in 2 hours at 200-210° C. and stirred at 220-250° C. for 13 hours to obtain a polyetherester polyol with an acid number of 2 mg KOH/g.

What is claimed is:

1. A composition of polymer or oligomer comprising the units of norbornanyl ester represented by the general Formula-1:

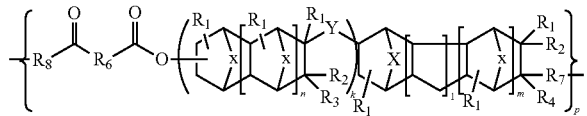

Formula-1 wherein, R$_1$ is a hydrogen atom, a methyl, or a hydroxymethyl group and R$_2$, R$_3$, and R$_4$ are the same or different from each other and are independently selected from the group consisting of hydrogen; halogen; hydroxyl; acid (—C(O)OH); ester (—C(O)OR$_a$); formate (—OC(O)H); acid halide (—C(O)Z); aldehyde (—C(O)H); ketone (—C(O)R$_a$); nitro (—NO$_2$); carboxamide (—C(O)NR$_a$R$_b$); amine (—NR$_a$R$_b$); silicone (—SiR$_a$R$_b$R$_c$); cyano (—CN); isocyanate (—NCO); alkoxy (—OR$_a$); phosphonate (—P(O)R$_a$R$_b$); unsubstituted or substituted C$_1$-C$_{100}$ alkyl group, unsubstituted or substituted C$_2$-C$_{100}$ alkenyl group, unsubstituted or substituted C$_2$-C$_{100}$ alkynyl group, unsubstituted or substituted C$_3$-C$_{100}$ cycloalkyl group, unsubstituted or substituted C$_6$-C$_{100}$ aryl group, provided that when it is substituted with one or more substituent groups, the substituent group may be carboxyl, hydroxyl, thiol, halogen, ester, amine, amide, imide, isocyanate, alkyl, alkenyl, alkynyl, haloalkyl, haloalkenyl, haloalkynyl, aryl, haloaryl, aralkyl, haloaralkyl, alkoxy, haloalkoxy, halocarbonyloxy, aryloxy, haloaryloxy, silyl, siloxy, glycidoxy, heterocyclo, carbonate, carboxylate, or quaternary ammonium; with the proviso that at least one of R$_2$, R$_3$, and R$_4$ is a polar functional group containing at least one atom selected from the group consisting of oxygen, nitrogen, phosphorus, sulfur, silicon and boron; R$_2$, R$_3$, and R$_4$ may be an acid anhydride group (—C(O)—O—C(O)—)

or an imide group (—C(O)—NR$_d$—C(O)—) formed by being bonded to each other when they are the functional groups;

X represents oxygen, CH$_2$, or CH$_2$—CH$_2$;

k is an integer of 0 to 100; l is an integer 0 to 1; m and n both represent an integer 0 to 5; p is an integer 1 to 1000;

Y is a bridge member selected from the group consisting of (—C(O)O—), (—R$_6$—), (—R$_7$C(O)O—), (—C(O)OR$_7$O—), (—C(O)OR$_7$OC(O)—), (—O—), (—OR$_7$O—), (—R$_7$OC(O)OR$_8$—), (—R$_7$C(O)OR$_8$—), and (—R$_7$C(O)R$_8$—);

R$_a$, R$_b$ and R$_c$ are independent hydrocarbyl or substituted hydrocarbyl,

R$_d$ is a hydrocarbyl group substituted with hydroxyl, alkoxy, alkenyl, amine, amide or imide group;

Z is a halogen atom;

R$_6$, R$_7$ and R$_8$ are divalent organic groups and may be substituted or unsubstituted alkanes, alkenes, or cycloaliphatic groups.

2. A process of producing a functional polymer containing a norbornane bridged ring according to claim 1, comprising the reaction of a functional norbornanyl ester derivative represented by the general Formula-2 with a reactive compound containing at least one group selected from hydroxyl, thiol, ester, epoxy, amine, alkenyl, alkynyl, norbornenyl, to produce a saturated or unsaturated polymer containing a terminal acrylate, hydroxyl, carboxyl, amine, epoxy, isocyanate, vinyl, or ester group, wherein the synthesis of norbornanyl ester monomer and polymerization may be carried out without isolation of the intermediate products in a one-pot process.

Formula-2

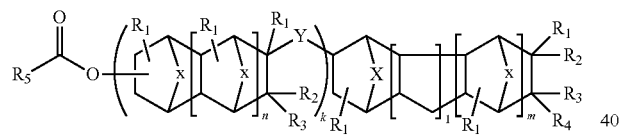

3. The process of producing a polymer according to claim 1 containing a norbornanyl lactone group of the general Formula-3, comprising a self-addition (lactonization) reaction of norbornene diacid in a one-pot process with maleic acid as acid catalyst, wherein the resulting lactone acid mixture can be used for production of ester compound or polymer in a one-pot process, and

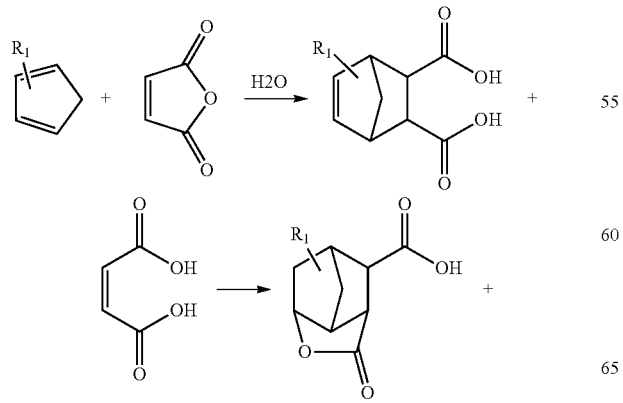

-continued

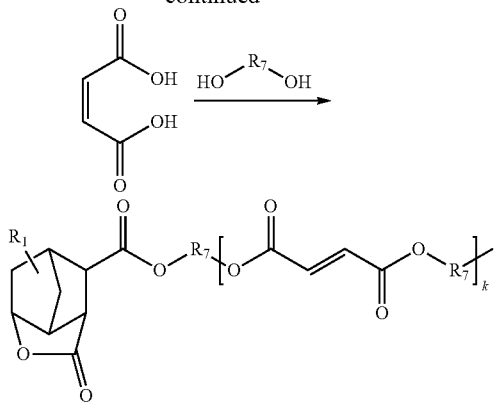

wherein the definitions of R$_1$, R$_7$ and k are the same as those in Formula-2.

4. The polymer according to claim 1, which is represented by the Formula-4:

Formula-4

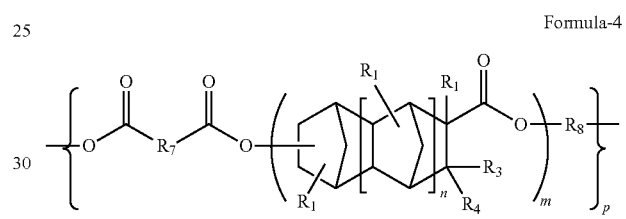

wherein the definitions of R$_{1-8}$, m, p and n are the same as those in Formula-1.

5. The polymer according to claim 1, which is represented by the Formula-5:

Formula-5 wherein the definitions of R$_{1-8}$, p and n are the same as those in Formula-1.

6. The polymer according to claim 1, which is represented by the Formula-6:

Formula-6 wherein the definitions of R$_{1-8}$, m and n are the same as those in Formula-1.

7. The compound according to claim 1, which is represented by the Formula-7:

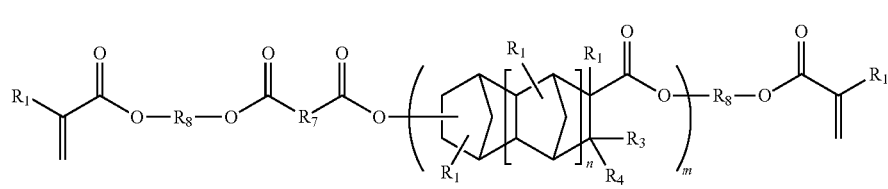

Formula-7 wherein the definitions of $R_{1-8}$, m and n are the same as those in Formula-1.

8. The polymer according to claim 1, which is represented by the Formula-8:

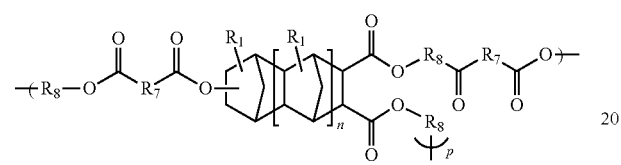

Formula-8 wherein the definitions of $R_{1-8}$, p and n are the same as those in Formula-1.

9. The polymer according to claim 1, which is represented by the Formula-9:

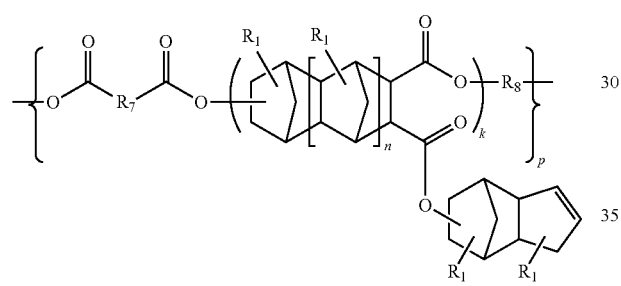

Formula-9 wherein the definitions of $R_{1-8}$, n, k and p are the same as those in Formula-1.

10. The polymer according to claim 1, which is represented by the Formula-10:

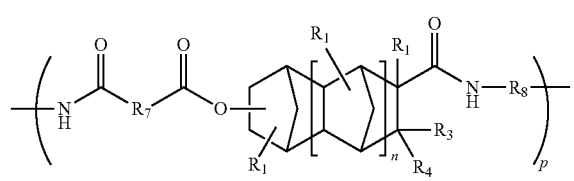

Formula-10 wherein the definitions of $R_{1-8}$, p and n are the same as those in Formula-1.

* * * * *